United States Patent
Claudio et al.

(10) Patent No.: US 9,316,632 B2
(45) Date of Patent: *Apr. 19, 2016

(54) METHODS OF SCREENING CHEMOTHERAPEUTIC AGENTS AND TREATING CANCER

(71) Applicant: Marshall University Research Corporation, Huntington, WV (US)

(72) Inventors: Pier Paolo Claudio, Huntington, WV (US); Jagan Valluri, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,292

(22) Filed: Mar. 19, 2013

(65) Prior Publication Data

US 2013/0295198 A1 Nov. 7, 2013

Related U.S. Application Data

(63) Continuation-in-part of application No. 12/405,944, filed on Mar. 17, 2009, now Pat. No. 8,993,231.

(60) Provisional application No. 61/612,771, filed on Mar. 19, 2012.

(51) Int. Cl.
*G01N 33/50* (2006.01)
*C12N 5/095* (2010.01)

(52) U.S. Cl.
CPC .......... *G01N 33/5014* (2013.01); *C12N 5/0695* (2013.01); *G01N 33/5011* (2013.01); *C12N 2503/02* (2013.01); *C12N 2525/00* (2013.01)

(58) Field of Classification Search
None
See application file for complete search history.

(56) References Cited

U.S. PATENT DOCUMENTS

| | | | | |
|---|---|---|---|---|
| 5,484,612 | A * | 1/1996 | Brown | 424/649 |
| 6,001,642 | A | 12/1999 | Tsao | |
| 2005/0244494 | A1* | 11/2005 | Wang et al. | 424/468 |
| 2006/0148078 | A1* | 7/2006 | Gerecht-Nir et al. | 435/366 |
| 2010/0062435 | A1 | 3/2010 | Claudio et al. | |

FOREIGN PATENT DOCUMENTS

| | | | | |
|---|---|---|---|---|
| EP | 1792979 | A1 * | 6/2007 | C12N 5/06 |
| EP | 2265708 | A2 | 9/2009 | |
| WO | WO 2007027938 | A1 * | 3/2007 | C12M 3/06 |

OTHER PUBLICATIONS

Kelly et al., The effects of microgravity on stem cell differentiation, Gravitational and Space Biology 21(1), 2007, 18.*
Yuge et al., Microgravity Potentiates Stem Cell Proliferation While Sustaining the Capability of Differentiation, Stem Cells and Development, 15:921-929 (2006).*
Grimm et al., Simulated microgravity alters differentiation and increases apoptosis in human follicular thyroid carcinoma cells, The FASEB Journal, 604-606, 2002.*
Gonda et al., Hydrofocusing Bioreactor for Three-Dimensional Cell Culture, NASA Tech Briefs, 2003, 53-54.*
Suto et al., MTT Assay With Reference to the Clinical Effect of Chemotherapy, Journal of Surgical Oncology 42:28-32 (1989).*
Soltysova et al., Cancer stem cells, Neoplasma, 52, 6, 2005, 435-440.*
Asazum T, et al., "Clinical features associated with recurrence of tumours of the spinal cord and cauda equina," Spinal Cord, Feb. 2003, vol. 41, p. 85-89.
Ballard KS, et al., "Embryonal rhabdomyosarcoma: adjuvant and ex vivo assay-directed chemotherapy," Int J Gynecol Cancer, May 2010, vol. 20, pp. 561-563.
Biddle A, et al., "Cancer stem cells and EMT in carcinoma," Cancer Metastasis Rev, Feb. 3, 2012, pp. 385-293.
Breidenbach M, et al., "Individualized long-term chemotherapy for recurrent ovarian cancer after failing high-dose treatment." Anticancer Drugs, Feb. 2002, vol. 13, pp. 173-176.
Brower SL, et al.,"The ChemoFx assay: an ex vivo chemosensitivity and resistance assay for predicting patient response to cancer chemotherapy," Methods Mol Biol, 3008, vol. 414, pp. 57-78.
Chen KL, et al., "Highly enriched CD133(+)CD44 (+) stem-like cells with CD133+CD44high metastatic subset in HCT116 colon cancer cells," Clin Exp Metastasis, Dec. 2011, vol. 28, pp. 751-763.
Cooper IS, et al., "Tumors of the spinal cord; primary extramedullary gliomas," Surg Gynecol Obstet 92, Feb. 1951, pp. 183-190.
Cree IA, et al., "Correlation of the clinical response to chemotherapy in breast cancer with ex vivo chemosensitivity," Anticancer Drugs, Aug. 1996, vol. 7, pp. 630-635.
Dalerba P, et al., "Phenotypic characterization of human colorectal cancer stem cells," Proc Natl Acad Sci U S A, Jun. 12, 2007, vol. 104, No. 24, 10158-10163.
Dave B, et al., "Epithelial-mesenchymal transition, cancer stem cells and treatment resistance," Breast Cancer Res, 2012, 4:202.

(Continued)

*Primary Examiner* — Galina Yakovleva
*Assistant Examiner* — Andrea S Grossman
(74) *Attorney, Agent, or Firm* — Stites & Harbison, PLLC; Terry L. Wright

(57) ABSTRACT

Methods for selecting chemotherapeutic agents for treating a cancer are provided that include the steps of providing a cancer cell sample having a population of bulk cancer cells and a population of cancer stem-like cells, culturing a first portion of the cancer cell sample in a hydrodynamic focusing bioreactor under microgravity conditions and for a period of time to selectively enhance the population of cancer stem-like cells and selectively kill the population of bulk cancer cells, contacting the cancer stem-like cells with one or more chemotherapeutic agents, and then selecting the one or more chemotherapeutic agents for treating the cancer if there is an increase in an amount of cytotoxicity. Methods for treating a cancer are also provided in which the identified chemotherapeutic agents are administered to a subject. Further provided are methods for identifying a test compound useful for treating a cancer.

37 Claims, 29 Drawing Sheets

(56) References Cited

OTHER PUBLICATIONS

Gallion H, et al.; "Progression-free interval in ovarian cancer and predictive value of an ex vivo chemoresponse assay," Int J Gynecol Cancer, 2006, vol. 16, 194-201.
Ghiaur G, et al., "Concise review: cancer stem cells and minimal residual disease," Stem Cells, Jan. 2012, vol. 30, pp. 89-93.
Herzog TJ, et al., "Chemosensitivity testing with ChemoFx and overall survival in primary ovarian cancer," Am J Obstet Gynecol, Jul. 2010, 203:68 e1-6.
Huh WK, et al., "Consistency of in vitro chemoresponse assay results and population clinical response rates among women with endometrial carcinoma," Int J Gynecol Cancer, Apr. 2011, vol. 21, No. 3, pp. 494-499.
Kawabata Y, et al., "Long-term outcome in patients harboring intracranial ependymoma," J Neurosurg, Jul. 2005, vol. 103, 31-37.
Kelly PN, et al., "Tumor growth need not be driven by rare cancer stem cells," Science, Jul. 20, 2007, vol. 317, p. 337.
Kelly PN, et al., "Rapid selection and proliferation of CD133+ cells from cancer cell lines: chemotheraperutic implications," 3PLoS One 5, 2010, e10035.
Kleinhans R, et al., "Sensor-based cell and tissue screening for personalized cancer chemotherapy," Med Biol Eng Comput, Jan. 31, 2012. vol. 50, pp. 117-126.
Kurbacher CM, et al., "Chemosensitivity testing using microplate adenosine triphosphate-based luminescence measurements," Methods Mol Med, 2005, 110, 101-120.
Lee Ke, et al., "From stem cells to cancer stem cells: HIF takes the stage," Curr Opin Cell Biol, 2012, vol. 24, pp. 232-235.
Li Y, et al., "Cancer stem cells: distinct entities or dynamically regulated phenotypes?" Cancer Res, 2012, vol. 72, No. 3, pp. 576-580.
Malik B, et al., "Cancer stem cells and resistance to chemo and radio therapy," Front Biosci (Elite Ed) 4, 2142 (2012).
Mi Z, et al., "Feasibility assessment of a chemoresponse assay to predict pathologic response in neoadjuvant chemotherapy for breast cancer patients," Anticancer Res, 2008, vol. 28, 1733-1740.
Michalova E, et al., "[Chemosensitivity prediction in tumor cells ex vivo-difficulties and limitations of the method]," Klin Onkol, 2008, vol. 21, No. 3 , pp. 93-97. See English abstract.
Myatt N, et al., "The ex vivo chemosensitivity profile of choroidal melanoma," Anticancer Drugs, Sep. 1997, vol. 8, pp. 756-762.
Ness RB, et al., "Cell viability assay for drug testing in ovarian cancer: in vitro kill versus clinical response," Anticancer Res, 2002, vol. 22, pp. 1145-1150.
Nguyen LV, et al., "Cancer stem cells: an evolving concept," Nat Rev Cancer, 2012, vol. 12, pp. 133-143.
Ochs RL, et al., "The ChemoFx assay: an ex vivo cell culture assay for predicting anticancer drug responses," Methods Mol Med, 2005, 110, 155-172.

Rice SD, et al., "An in vitro chemoresponse assay defines a subset of colorectal and lung carcinomas responsive to cetuximab," Cancer Biol Ther, Jan. 2011, vol. 11, No. 2, pp. 196-203.
Rice SD, et al., "Analysis of chemotherapeutic response heterogeneity and drug clustering based on mechanism of action using an in vitro assay," Anticancer Res, Jul. 2010, vol. 30, 2805-2812.
Ricci-Vitiani L, et al., "Identification and expansion of human colon-cancer-initiating cells," Nature, 2007, vol. 445, pp. 111-115.
Suchy SL, et al., "Chemoresponse assay for evaluating response to sunitinib in primary cultures of breast cancer," Cancer Biol Ther, 2011, vol. 11, No. 12, 1059-1064.
Tsubouchi H, et al., "Sensitivity of human pancreatic adenocarcinoma tumor lines to chemotherapy, radiotherapy, and hyperthermia," Hum Cell, Dec. 2000, vol. 13, No. 4, pp. 203-212.
Vandertop WP, "Spinal cord ependymoma: radical surgical resection and outcome," Neurosurgery, Correspondence, Jul. 2003, vol. 53, pp. 246.
Van Meerlo J, et al., "Cell sensitivity assays: the MTT assay," Methods Mol Biol, 2011, vol. 731, pp. 237-245.
Yu Y, et al., "The role of cancer stem cells in relapse of solid tumors," Front Biosci (Elite Ed), 2012, vol. 4, pp. 1528.
EPO, European Examination Report for related European patent application No. EP 09 72 1750.9, issued Aug. 26, 2013.
Chung et al., "Human Embryonic System Cell Lines Generated without Embryo Destruction," Cell Stem Cell 2, Feb. 2006, pp. 113-117.
Bansal et al., "Tumor initiating cells," Current Pharmaceutical Biotechnology, Feb. 2009, vol. 10, No. 2, pp. 192-196.
Jones, Richard J., "Cancer stem cells clinical relevance," Journal of Molecular Medicine, Oct. 2009, vol. 87, No. 11, pp. 1105-1110.
Small et al., "Maintenance of telomeres in SV40-tranformed pre-immortal and immortal human fibroblasts," Journal of cellular Physiology, Sep. 1996, vol. 168, No. 3, pp. 727-736.
Shay et al., "Use of telomerase to create bioengineered tissues," Annals of the New York Academy of Sciences, Dec. 2005, vol. 1057, pp. 479-491.
Hanbali F et al., Spinal Cord Ependymoma: Radical Surgical Resection and Outcome, Neurosurgery, Nov. 2002, vol. 51, No. 5, pp. 1162-1174.
Dylla DP et al., "The New Look of Colorectal Cancer Stem Cells," Gastroenterology, Apr. 2008, vol. 134, No. 4, pp. 1262-1264.
Kennedy JA et al., "Tumor Growth Need Not be Driven by Rare Cancer Stem Cells," Science, Technical Comment, Dec. 2007, vol. 318, 1722c.
Boop FA, "Long-term outcome in patients harboring intracranial ependymoma," J Neurosurg, Editorial, 2005, vol. 103, pp. 4-5.
Palma L, "Ependymoma," J. Neurosurg., Letters to the editor, 2006, vol. 105,, pp. 503-504.

* cited by examiner

METHODS OF SCREENING CHEMOTHERAPEUTIC AGENTS AND TREATING CANCER

RELATED APPLICATIONS

This application is a Continuation-In-Part of U.S. application Ser. No. 12/405,944, and claims priority from U.S. Provisional Application Ser. No. 61/612,771, filed Mar. 19, 2012, the entire disclosures of which are incorporated herein by this reference.

GOVERNMENT INTEREST

This invention was made with government support under Grant Nos. CA131395, CA140024, UL1RR033173, 5P20RR020180, and WV-INBRE 5P20RR016477 awarded by the National Institutes of Health. The government has certain rights in the invention.

TECHNICAL FIELD

The presently-disclosed subject matter relates to methods of selecting chemotherapeutic agents for treating a cancer, as well as methods of treating cancer by administering the selected chemotherapeutic agents to a subject in need thereof. In particular, the presently-disclosed subject matter relates to methods where a cancer cell sample is cultured in a hydrodynamic focusing bioreactor to selectively enhance a population of cancer stem-like cells, such that it can be determined whether one or more chemotherapeutic agents are cytotoxic to the cancer stem-like cells and an appropriate treatment regimen can be selected.

BACKGROUND

Administration of ineffective anti-cancer therapy is associated with unnecessary toxicity and development of resistant clones. Indeed, each time cancer patients are treated, those individuals have a high chance of relapse and encounter a significant risk that their cancer may become more resistant to therapy. In this regard, attempts have been made over the years to develop an ex-vivo anti-cancer test that would provide clinically-relevant treatment information. However, due to the presence of cancer stem-like cell populations in a number of types of human cancer, which comprise only a small subset of the cancer cells within each cancerous tumor, but yet retain their stem cell properties of self-renewal and differentiate into phenotypically heterogeneous [4-12], aberrant progeny, an ex-vivo anti-cancer test capable of identifying treatment regimens that minimize toxicity and prevent the development of resistant clones has yet to be developed.

It has been observed that unlike the bulk of tumor cells, cancer stem-like cells frequently resist chemotherapy, and thereby cause a relapse of the disease [9, 10, 12]. Indeed, this resistance of the cancer stem-like cells can cause chemotherapeutic treatments to be ineffective and associated with unnecessarily high toxicity or the development of resistant clones. In certain types of cancer where neoplastic growth depends on cancer stem-like cells, it is thought that the eradication of the cancer stem-like cell population may be curative or may provide an effective complement to traditional treatment approaches such as surgery, chemotherapy, and/or radiation therapy. Presently, however, chemotherapeutic agent testing is still performed only on cancer cells from patients without prior separation and proliferation of the often chemotherapy-resistant cancer stem-like cells from the bulk cancer cells [39, 52-63]. Thus, there remains a need for a method that identifies an effective chemotherapeutic agent for a particular cancer that would eliminate both the cancer's bulk cancer cells and cancer stem-like cells. Such methods would be both highly desirable and beneficial for, among other things, cancer research and personalized anti-cancer treatments.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a method for selecting one or more chemotherapeutic agents for treating a cancer is provided that comprises the steps of: providing a cancer cell sample including a population of bulk cancer cells and a population of cancer stem-like cells; culturing a first portion of the cancer cell sample (e.g., $1 \times 10^6$ cells) in a hydrodynamic focusing bioreactor under microgravity conditions and for a period of time sufficient to selectively enhance the population of cancer stem-like cells and selectively kill the population of bulk cancer cells; contacting the cancer stem-like cells with one or more chemotherapeutic agents; determining whether the one or more chemotherapeutic agents are cytotoxic to the cancer stem-like cells; and then selecting the one or more chemotherapeutic agents to treat the cancer if there is an increase in an amount of cytotoxicity. In some embodiments, the method further includes culturing a second portion of the cancer cell sample (e.g., $1 \times 10^6$ cells) under conditions and for a period of time sufficient to enhance the bulk cancer cells, and then contacting the bulk cancer cells with the one or more chemotherapeutic agents to determine whether the one or more chemotherapeutic agents are cytotoxic to the bulk cancer cells. In some embodiments, the one or more chemotherapeutic agents are then selected for treating the cancer based on their cytotoxicity to both the cancer stem-like cells and the bulk cancer cells.

In some embodiments of the methods for selecting a chemotherapeutic agent, a method is provided that further includes the step of identifying a type of bulk cancer cells such that the one or more chemotherapeutic agents are further selected based on the type of bulk cancer cells present in the cancer cell sample. In some embodiments, the cancer cell sample is immunophenotyped so as to identify a type of cancer cell in the cancer cell sample. In some embodiments, the immunophenotyping is performed by flow cytometry techniques using one or more antibodies against the cancer cell sample, such as, for example by using antibodies against CD24, CD34, CD38, CD44, CD133, CXCR4, OCT3/4, Nanog, or combinations thereof.

With regard to the step of contacting the cancer cells with one or more chemotherapeutic agents, in some embodiments, the step of contacting the cancer stem-like cells with the one or more chemotherapeutic agents comprises contacting the cancer stem-like cells with the one or more chemotherapeutic agents for a time period of about one hour. In some embodiments, the step of contacting the cancer stem-like cells with one or more chemotherapeutic agents comprises contacting the cancer stem-like cells with a predetermined concentration of the one or more chemotherapeutic agents that comprises a concentration below a clinically relevant dosage, a concentration equal to the clinically relevant dosage, or a concentration above the clinically relevant dosage for a particular chemotherapeutic agent. In some embodiments, the one or more chemotherapeutic agents are selected from cisplatin, oxaliplatin, arabinoside-C, etoposide (VP-16), busulfan, methotrexate, irinotecan (CPT-11), temozolomide, and combinations thereof.

Subsequent to contacting the cancer cells with one or more chemotherapeutic agents, in some embodiments, a percentage of non-viable cancer stem-like cells is then calculated to determine whether the one or more chemotherapeutic agents are cytotoxic to the cancer stem-like cells. In some embodiments, the percentage of non-viable cancer stem-like cells is calculated using an MTT assay, the results of which can then be used to select a chemotherapeutic agent for treating the cancer being tested.

In some embodiments, the cancer cell sample that is provided comprises a solid cancer cell sample, a liquid cancer cell sample, or combinations thereof. In some embodiments, the solid cancer cell sample comprises, for example, a lung cancer cell sample, a breast cancer cell sample, a central nervous system cancer cell sample, a colon cancer cell sample, or combinations thereof. In some embodiments, the liquid cancer cell sample comprises, for example, a leukemia cell sample, a lymphoma cell sample, or a myeloma cell sample.

Further provided, in some embodiments of the presently-disclosed subject matter, are methods for treating a cancer. In some embodiments, a method for treating a cancer is provided that comprises the steps of providing a cancer cell sample from the subject that includes a population of bulk cancer cells and a population of cancer stem-like cells; culturing a first portion of the cancer cell sample in a hydrodynamic focusing bioreactor under microgravity conditions and for a period of time sufficient to selectively enhance the population of cancer stem-like cells and selectively kill the population of bulk cancer cells; contacting the cancer stem-like cells with one or more chemotherapeutic agents; determining whether the chemotherapeutic agents are cytotoxic to the cancer stem-like cells; selecting the chemotherapeutic agents for treating the cancer if there is an increase in an amount of cytotoxicity; and then administering the selected chemotherapeutic agents to the subject to treat the cancer in the subject.

Still further provided, in some embodiments of the presently-disclosed subject matter are screening methods for identifying a compound useful for treating a cancer. In some embodiments, a method of identifying a compound as useful for treating a cancer is provided that comprises the steps of: providing a cancer cell sample including a population of bulk cancer cells and a population of cancer stem-like cells; culturing the cancer cell sample in a hydrodynamic focusing bioreactor under microgravity conditions and for a period of time sufficient to selectively enhance the population of cancer stem-like cells and selectively kill the population of bulk cancer cells; contacting the cancer cell sample with an effective amount of a test compound; determining whether the test compound is cytotoxic to the cancer stem-like cells; and identifying the test compound as a compound useful for treating cancer if there is an increase in cytotoxicity subsequent to contacting the cells with the test compound.

Further advantages of the presently-disclosed subject matter will become evident to those of ordinary skill in the art after a study of the description, Figures, and non-limiting Examples in this document.

DESCRIPTION OF EXEMPLARY EMBODIMENTS

Figure 1A:
FIGS. 1A-1C are images of a magnetic resonance imaging (MRI) diagnostic scan and hematoxylin and eosin staining of an anaplastic ependymoma, including: an MRI image of the cervical spine of a subject showing the presence of an enhancing mass, which extends from mid C5 to inferior C7 (4.5 in length×1.0×2.0 in cephalocaudal and anteroposterior dimension) and causing cord compression (FIG. 1A); an MRI image of the thoracic spine of the subject showing an enhancing lesion at T2-3 (1.5 in length×0.6×0.6 cm in anteroposterior and transverse dimension) with several other smaller nodular masses, best seen on the T2 weighted sequence, which extended throughout the thoracic level to T11 (FIG. 1B); and an image showing hematoxylin and eosin staining of a tumor section showing an overall predominant dense cellular component, with primitive nuclear features, mitotic activity, necrosis and vascular proliferation, where the presence of well formed, obvious perivascular pseudorosettes (with vasocentric pattern, perivascular nuclear-free zones, and classic thin glial processes radiating to/from the vessel wall) were found supportive of the diagnosis of intradural, extramedullary anaplastic diffuse spinal ependymoma, WHO grade 3 (FIG. 1C)

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes methods for selecting one or more chemotherapeutic agents for treating a cancer, as well as methods of treating a cancer in a subject by administering the one or more selected chemotherapeutic agents to the subject.

In some embodiments of the presently-disclosed subject matter, a method of selecting one or more chemotherapeutic agents for treating a cancer is provided that comprises the steps of: (1) providing a cancer cell sample that includes a population of bulk cancer cells and a population of cancer stem-like cells; (2) culturing a first portion of the cancer cell sample in a hydrodynamic focusing bioreactor under microgravity conditions and for a period of time sufficient to selectively enhance the population of cancer stem-like cells and selectively kill the population of bulk cancer cells; (3) contacting the cancer stem-like cells with one or more chemotherapeutic agents; (4) determining whether the one or more chemotherapeutic agents are cytotoxic to the cancer stem-like cells; and (5) selecting the one or more chemotherapeutic agents for treating the cancer if there is an increase in an amount of cytotoxicity subsequent to contacting the cancer stem-like cells with the one or more chemotherapeutic agents.

As used herein, the term "cancer" is used to refer to all types of cancer or neoplasm or malignant tumors found in a subject, including leukemias, lymphomas, myelomas, carcinomas (e.g., adenocarcinomas), melanomas, teratomas, and sarcomas. Examples of cancers include cancer of the liver, pancreas, esophagus, bladder, breast, central nervous system (e.g., spine or brain), cervix, colon, rectum, head and neck, kidney, lung, ovary, prostate, sarcoma, stomach, uterus, leukemias, lymphomas, myelomas, and melanomas. In some embodiments of the presently-disclosed subject matter, the cancers described herein are divided into two general classes, namely "solid tumors," or cancers that are formed of solid tissue, and "liquid cancers," or cancers found in an aqueous biological sample, such as those cancers that travel in the blood stream.

The term "cancer cell sample" is used herein to refer to a sample of cancer cells that have been obtained and/or are otherwise provided from cancerous tissue of a subject. Such cancer cell samples can include primary cell culture samples obtained directly from a cancer of a subject, or can include an established cell culture that has been derived from a cancer in a subject, such as those that can be purchased from cell repositories. In some embodiments, the cancer cell sample comprises a solid cancer cell sample, a liquid cancer cell sample, or combinations thereof. In some embodiments, the cancer cell sample is a solid cancer cell sample that comprises, in some embodiments, a lung cancer cell sample, a breast cancer cell sample, a central nervous system cancer cell sample, a colon cancer cell sample, a metastatic lymph node cell sample, or combinations thereof. In other embodiments, the cancer cell sample is a liquid cancer cell sample that comprises, in some embodiments, a leukemia cell sample, a lymphoma cell sample, a myeloma cell sample, or combinations thereof.

Regardless of the particular type of cancer cell sample obtained and/or provided from a subject, as noted above, each cancer cell sample generally comprises a population of bulk cancer cells and a population of cancer stem-like cells. As would be recognized by those skilled in the art, and according to cancer stem cell theory, tumors are typically not comprised of simple monoclonal expansions of transformed cells, but are complex tissues where abnormal growth originates from a pathological minority of cancer stem-like cells. These cells maintain stem-like characteristics in that they proliferate very slowly and have an inherent capacity to self-renew and differentiate into phenotypically heterogeneous, aberrant progeny. Cancer stem-like cells possess the capacity to self-renew and to cause the heterogeneous lineage of the bulk cancer cells that comprise the cancer cell sample, or the cancer as a whole. The cancer stem-like cells have the ability to initiate tumors when implanted in a subject, and the cells can theoretically originate from stem cell or progenitor or differentiated cells that de-differentiate into stem-like cells. As such, the term cancer stem-like cell is used interchangeably herein with the terms "cancer stem cell," "tumor-initiating cell," "cancer-initiating cell," or other similar terms used in the art, to refer to a subset of cancer cells within each tumor that exhibit stem cell-like characteristics and are capable of initiating tumor growth in a subject. The term "bulk cancer cells" is thus used herein to refer to the remainder of the cells in the tumor, which typically exhibit unusually rapid growth, exhibit varying levels of differentiation, and typically account for the majority of a tumor or cancer sample's mass.

In some embodiments of the presently-disclosed methods, the selection of a chemotherapeutic agent for treating a cancer begins by providing a cancer cell sample that includes a population of bulk cancer cells and a population of cancer stem-like cells. As used herein, the term "providing" is used to refer to the gathering of a cancer cell sample, the receipt of a cancer cell sample to be tested, or both. In this regard, in some embodiments, the step of providing a cancer cell sample is used to refer to a step by which a cancer cell sample is obtained from a patient, for example, by collecting a biopsy of a cancer from a subject. In other embodiments, the step of providing a cancer cell sample is used to refer to means by which a cancer cell sample is received and/or otherwise provided for subsequent testing. For example, in certain embodiments, the step of providing a cancer cell sample refers to a physician obtaining a cancer cell sample from a subject and/ or refers to a laboratory technician who obtains the cancer cell sample for testing.

As noted, upon providing the cancer cell sample, a first portion of the cancer cell sample is then cultured in a hydrodynamic focusing bioreactor (HFB) under microgravity conditions and for a period of time sufficient to selectively enhance the population of cancer stem-like cells. The term "hydrodynamic focusing bioreactor" is used herein to refer to a bioreactor, e.g., vessel for growing cells or organisms, that relies on the principle of hydrodynamic focusing to control the movement of contents within the culture chamber of the bioreactor. "Hydrodynamic focusing" refers to the force of liquid in motion used to control the movement of contents within the culture chamber of the bioreactor. In some embodiments, the HFB is a horizontally-rotating, fluid filled culture vessel equipped with a membrane for diffusion gas exchange to optimize gas/oxygen-supply capable of simulating microgravity. In the HFB, at any given time, gravitational vectors are randomized and the shear stress exerted by the fluid on any synchronously moving particles (e.g., cultured cells) is minimized, such that the HFB offers a unique hydrodynamic focusing capability that enables the creation of a low-shear culture enforcement simultaneously with the herding of suspended cells, tissue assemblies, and air bubbles. For additional information and guidance regarding the HFB and the culturing of cells therein, see, e.g., U.S. Pat. No. 6,001,642 and U.S. Patent Application Publication No. 2010/0062435, each of which is incorporated herein by this reference.

The term "microgravity," as used herein, refers to near weightlessness that, for example, may be created inside a spacecraft as it orbits the Earth. Due to microgravity within a HFB, there is no buoyancy, no convection, no stratification of layers, and where surface tension dominates, major impacts on metabolism will be reflected in the biosynthetic potential of cultured cells. This is in contrast to "normal gravity" or "static conditions," by which is meant the normal or usual gravitational force exerted on earth in a gravity-unmanipulated environment, also represented as "1G" or "1g."

In some embodiments of the presently-disclosed subject matter, and as also described in U.S. Patent Application Publication No. 2010/0062435, the microgravity conditions within the HFB, along with other conditions such as pressure and temperature, are tailored to provide a culture environment that selectively enhances (e.g., increases or enriches) an amount of cells in the cancer stem-like cell population of the cancer cell sample, while selectively killing the bulk cancer cells in the cancer cell sample. For example, in some embodiments, culturing the cancer cell sample in the HFB can be used to selectively enhance a cancer stem-like cell population and selectively kill a bulk cancer population in a particular cancer cell sample (e.g., an ependymoma cancer cell sample)

such that a primary culture that comprises only 45.5% CD133 (+) cells is transformed into a culture of cells that comprises 95.93% CD133(+) cells after 10 days of culture in a HFB.

In some embodiments, the cancer stem-like cells in the cancer cell sample are enriched by manipulating HFB culture parameters, by incubating cells in an ozone rich environment or in a plasma gas rich environment, or by effecting conditions that alter an oxidation-reduction (i.e., redox) status of the cells cultured in the HFB. In some embodiments, the cellular redox environment inside a HFB can be influenced by the production and removal of reactive oxygen species (ROS), such that the cellular ROS level can function as second messengers regulating numerous cellular processes (e.g., proliferation) and such that the cancer stem-like cell can take advantage of the aberrant redox system and spontaneously proliferate. For example, in some embodiments, the cancer stem-like cells cultured in the HFB are exposed for 2 to 6 hours with ozone ($O_3$) levels of 0.08 to 0.40 PPM to cause a fluctuation in the cellular redox environment, which is then believed to regulate cell cycle progression from quiescence (G0) to the proliferative (G1, S, G2, and M) cycle and back to the quiescent growth state. As another, example, in some embodiments, the cancer stem-like cells in the cancer cell sample are enhanced by manipulating HFB culture parameters, by incubating cells in a $CO_2$— and ozone-rich environment or in a plasma gas-rich environment, or by the addition of exogenous ROS($H_2O_2$) that drive, at least in part, the self-renewal and proliferation of cancer stem-like cells. In some embodiments, the cancer stem-like cells are seeded into the HFB along with media and $H_2O_2$ at concentrations of about 0 µM, about 1 µM, about 2 µM, about 3 µM, about 4 µM, about 5 µM, or about 10 µM.

Any desired number of cells may be cultured in a HFB in accordance with the presently-disclosed subject matter. In some embodiments, about $1 \times 10^3$ cells, about $1 \times 10^4$ cells, about $1 \times 10^5$ cells, or about $1 \times 10^6$ cells are cultured in the HFB. In some embodiments, about $1 \times 10^5$ cells are cultured in the HFB. Of course, the selection of an appropriate amount of cells to culture in an HFB can be selected for a particular application as necessary, and can be determined using only routine experimentation.

Turning now to the step of contacting the cultured cancer stem-like cells with one or more chemotherapeutic agents subsequent to culturing the cells in the HFB, the term "contacting" is used herein to refer any method by which a chemotherapeutic agent can be placed into contact with a cell, such as those in a cancer cell sample, and allowed to communicate (e.g., biochemically) or otherwise interact with the contacted cells. As would be recognized by those of ordinary skill in the art, numerous means can be used to contact a cell with a chemotherapeutic agent in accordance with the presently-disclosed subject matter, including, but not limited to: test tubes, culture dishes (e.g., a 96-well plate), and the like.

The term "chemotherapeutic agent" is used herein to refer to an agent that is capable of "treating" a cancer, as defined herein below. For example, the chemotherapeutic agent may kill cancer cells, prevent or inhibit the development of cancer cells, induce apoptosis in cancer cells, reduce the growth rate of cancer cells, reduce the incidence or number of metastases, reduce tumor size, inhibit tumor growth, reduce the blood supply to a tumor or cancer cells, promote an immune response against cancer cells or a tumor, prevent or inhibit the progression of cancer, or increase the lifespan of a subject with cancer.

Examples of chemotherapeutic agents include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE®; or YONDELIS®. In some embodiments, the chemotherapeutic agents used to contact the cells of the presently-disclosed subject matter are selected from cisplatin, oxaliplatin, arabinoside-C, etoposide (VP-16), busulfan, methotrexate, irinotecan (CPT-11), and temozolomide.

In some embodiments, the chemotherapeutic agent that is used to contact the cancer cells comprises a test compound to be analyzed for its ability to "treat" a cancer as defined herein below. As such, in some embodiments of the presently-disclosed methods, a method for screening additional agents for the treatment of a cancer is also provided, such that previously undiscovered therapeutic agents, known therapeutic agents not typically used for the treatment of a cancer, or other therapeutic agents can be assessed for their effects on cancer stem-like cells. For example, in some embodiments, a methods for screening a test compound for treating a cancer is provided that includes the steps of: providing a cancer cell sample including a population of bulk cancer cells and a population of cancer stem-like cells; culturing the cancer cell sample in a hydrodynamic focusing bioreactor under microgravity conditions and for a period of time sufficient to selectively enhance the population of cancer stem-like cells and selectively kill the population of bulk cancer cells; contacting the cancer cell sample with an effective amount of a test compound; determining whether the test compound is cytotoxic to the cancer stem-like cells; and identifying the test compound as a compound useful for treating cancer if there is an increase in cytotoxicity. In some embodiments, the cancer cell sample comprises a primary cell culture obtained from a cancer of a subject. In other embodiments, the cancer cell sample is an established cancer cell line.

In some embodiments of the presently-disclosed methods, contacting the cells with the one or more chemotherapeutic agents comprises contacting the cells with the agents for a predetermined time period. In some embodiments, the predetermined time period is about 10 minutes, about 20 minutes, about 30 minutes, about 40 minutes, about 50 minutes, about 60 minutes, about 70 minutes, about 80 minutes, about 90 minutes, about 100 minutes, about 2 hours, about 3 hours, about 4 hours, about 5 hours, about 6 hours about 8 hours, about 10 hours, about 12 hours, about 14 hours, about 16 hours, about 18 hours, about 20 hours, about 22 hours, or about 24 hours, or more. In some embodiments, the time period is about 1 hour. Of course, other time periods can also be chosen for a particular application or cancer cell sample, and can be identified using only routine experimentation.

In some embodiments of the methods, the step of contacting the cancer stem-like cells with the one or more chemotherapeutic agents comprises contacting the cancer stem-like cells with a predetermined concentration of the one or more chemotherapeutic agents. In some embodiments, the predetermined concentration of the one or more chemotherapeutic agents comprises a concentration below a clinically relevant dosage, equal to the clinically relevant dosage, or above the clinically relevant dosage. The term "clinically relevant dosage" is used herein to refer to a concentration of a chemotherapeutic that is calculated by body weight of a particular subject and that, when administered to a subject to treat a cancer, would be sufficient to achieve a desired biological response (i.e., an increase in an amount of cytotoxicity or other therapeutic effect in the subject).

Turning now to the step of determining whether the one or more chemotherapeutic agents are cytotoxic to the cancer stem-like cells, the term "determining," as used herein in reference to determining an amount of cytotoxicity, is used to refer to the measurement or assessment (e.g., quantitative and/or qualitative) of a particular chemotherapeutic agent's ability to kill or otherwise inhibit the proliferation of (i.e., exert a cytotoxic or cytostatic effect) of a target cell (e.g., a cancer stem-like cell) when the cell is contacted with the chemotherapeutic agent. In some embodiments, determining whether the particular chemotherapeutic agent exerts a cytotoxic effect includes calculating a percentage of cells killed (e.g., non-viable cancer stem-like cells) relative to the number of cells originally in a sample. In some embodiments, cytotoxicity is determined using an MTT assay, an ALAMARBLUE® Assay (Invitrogen, Carlsbad, Calif.), or a WST-8 assay, Cayman Chemical, Ann Arbour, Mich.), a CyQUANT assay (LifeTechnologies, Grand Island, N.Y.), any of which can be used to quantitatively measure the cytotoxic effects of the agent contacting the cell sample. In some embodiments, determining the cytotoxicity of an agent includes measuring one or more biomarkers of apoptosis or cell death in a sample of interest or includes measuring other molecules that can be used to measure an amount of viable and non-viable cells such as, for example, protease biomarkers. In some embodiments, cell death is determined using a trypan blue exclusion assay, which can also be used to quantitatively measure the cytotoxic effects of the agent contacting the cell sample.

With regard to the various methods of screening chemotherapeutic agents described herein, the skilled artisan will understand that measuring an increase in the amount of a cytoxicity (e.g., an increase in cell death) is a statistical analysis. For example, an increase in an amount of cytotoxicity in a cultured sample can be compared to a control level of cytotoxicity, and an amount of cytotoxicity of more than the control level can be indicative of an increase in the amount of cytotoxicity, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In some embodiments of the presently-disclosed subject matter, upon determination that there is an increase in an amount of cytotoxicity in a culture of cancer stem-like cells, the chemotherapeutic agent can then be selected for treating the cancer based on its cytotoxic effects on the one or more cancer stem-like cells. In some embodiments, the chemotherapeutic agent selected for treatment is further determined based on whether the chemotherapeutic agent is cytotoxic to both the cancer stem-like cells and the bulk cancer cells found in a particular cancer cell sample. In this regard, in some embodiments of the presently-disclosed methods, the methods further comprise the steps of: (1) culturing a second portion of the cancer cell sample (e.g., culturing about $1 \times 10^3$ cells) under conditions and for a period of time sufficient to enhance (e.g., increase the number of or enrich) the bulk cancer cells within the sample; (2) contacting the bulk cancer cells with the one or more chemotherapeutic agents; and (3) determining whether the one or more chemotherapeutic agents are cytotoxic to the bulk cancer cells such that the one or more chemotherapeutic agents can be selected for treating the cancer based on their activity against both the cancer stem-like cells and the bulk cancer cells. In some embodiments, selecting the one or more chemotherapeutic agents based on their activity against both the cancer stem-like cells and the bulk cancer cells thus limits the amount and types of chemotherapeutic agent or agents that must be administered and, in some embodiments, can increase the effectiveness of a chemotherapeutic agent administration.

In some embodiments, a more specific treatment and, consequently, a more appropriate and/or effective treatment is further selected by also characterizing or otherwise identifying the cells in the cancer cell sample. In this regard, in further embodiments of the presently-disclosed subject matter, the methods further comprise the step of immunophenotyping the cancer cell sample to identify a type of cancer cell in the cancer cell sample. The term "immunophenotyping" as used herein refers to classifying cells into groups based the expression of certain proteins by the cells. For example, in some embodiments, antibodies are used to identify cells by detecting specific antigens expressed by the cells, which are also referred to as markers. In some embodiments, the antibodies used are against the protein markers: CD24, CD34, CD38, CD44, CD117, Cd133, OCT3/4, Nanog, or combinations thereof. In some embodiments, the step of immunophenotyping the cancer cell sample is performed by flow cytometry using one or more antibodies against the cancer cell sample, such as one or more antibodies against the foregoing protein markers. In some embodiments, additional or alternative antibodies specific for other markers capable of identifying cancer stem-like cells can also be used without departing from the spirit and scope of the subject matter described herein.

Still further provided, in some embodiments of the presently-disclosed subject matter, are methods of treating a cancer in a subject in need thereof. In some embodiments, a method of treating a cancer is provided that comprises: providing a cancer cell sample from the subject that includes a population of bulk cancer cells and a population of cancer stem-like cells; culturing a first portion of the cancer cell sample in a hydrodynamic focusing bioreactor under microgravity conditions and for a period of time sufficient to selectively enhance the population of cancer stem-like cells and selectively kill the population of bulk cancer cells; contacting the cancer stem-like cells with one or more chemotherapeutic agents; determining whether the one or more chemotherapeutic agents are cytotoxic to the cancer stem-like cells; selecting the one or more chemotherapeutic agents for treating the cancer if there is an increase in an amount of cytotoxicity; and then administering the one or more selected chemotherapeutic agents to the subject to thereby treat the cancer.

The terms "treatment," "treating," and grammatical variations thereof are used herein to refer to any treatment of cancer, including but not limited to prophylactic treatment to prevent development of a cancer or reduce severity of a cancer's symptoms. As such, the terms treatment or treating include, but are not limited to: preventing cancer or the development of cancer; inhibiting the progression of cancer; arresting or preventing the development of cancer; reducing the severity of cancer; ameliorating or relieving symptoms associated with cancer; and causing a regression or eradication of cancer or one or more of the symptoms associated with cancer. In certain circumstances, the subject being "in need thereof" refers to a subject that has been diagnosed with a cancer comprising both bulk cancer cells and cancer stem-like cells, such that it is advisable to determine what chemotherapeutic agents are cytotoxic to both the bulk cancer cells and the cancer stem-like cells, and such that one or more chemotherapeutic agents can then be selected and administered to that particular subject.

For administration of a chemotherapeutic agent as disclosed herein, suitable methods for administering a chemotherapeutic agent in accordance with the methods of the presently-disclosed subject matter include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

Regardless of the route of administration, the chemotherapeutic agents are typically administered in an amount effective to achieve the desired response. As used herein, the terms "effective amount" and "therapeutically effective amount" refer to an amount of the chemotherapeutic agent sufficient to produce a measurable biological response (e.g., an increase in cytotoxicity in the cancer stem-like cells, bulk cancer cells, or both). Actual dosage levels of the chemotherapeutic agents can be varied so as to administer an amount of the chemotherapeutic agent that is effective to achieve the desired therapeutic response for a particular subject and/or application. Of course, the effective amount in any particular case will depend upon a variety of factors including the activity of the chemotherapeutic agent, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art and, in some embodiments, can be made using the methods described herein.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, New Jersey; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

The presently-disclosed subject matter thus permits the selection of a chemotherapeutic agent that can be used to treat a cancer notwithstanding the cancer including cancer stem-like cells that are resistant to certain chemotherapeutic agents, and whose presence causes many treatments to fail. The step of culturing the cancer stem-like cells within an HFB provides a relatively dense population of cancer stem-like cells that can be quickly and efficiently screened with a variety of chemotherapeutic agents. Furthermore, selecting chemotherapeutic agents that are cytotoxic to the bulk cancer cells as well as the cancer stem-like cells in a particular cancer cell sample allows ineffective chemotherapeutic agents to be eliminated from selection, thereby avoiding unnecessary toxicity during treatment, and thereby choosing the most effective chemotherapeutic agent that allows subjects to avoid the physical, emotional, and financial costs of failed treatment, while experiencing an increased quality of life.

As used herein, the term "subject" includes both human and animal subjects. Thus, veterinary therapeutic uses are also provided in accordance with the presently disclosed subject matter. As such, the presently-disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex. Thus, adult and newborn subjects, as well as fetuses, whether male or female, are intended to be covered.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Additionally, the following examples may include compilations of data that are representative of data gathered at various times during the course of development and experimentation related to the present invention.

EXAMPLES

Materials and Methods for Examples 1-5

Single Cell Suspension and Primary Cell Culture. Single-cell suspensions from the ependymoma biopsy was prepared using the gentleMACS™ Dissociator (Miltenyi, Auburn, Calif.), and C Tubes using a standardized, semi-automated protocol based on a combination of mechanical tissue disruption and incubation with a 50% solution 0.025% trypsin and Accutase (Innovative Cell Technologies, San Diego, Calif.). Cells were serially plated in 24-well, 12-well, 6-well, 10-cm treated dishes and cultured to subconfluence in RPMI-1640 medium supplemented with 5% irradiated, heat inactivated, defined fetal bovine serum (Thermofisher/Hyclone), and 50 U of penicillin and 5 µg of streptomycin/mL of medium (Thermofisher/Mediatech).

Three-Dimensional Bioreactor Cell Culture. A hydrodynamic focusing bioreactor (HFB) (Celdyne, Houston Tex.) was used as previously described to proliferate cancer stem-like cells [12]. Culture media, oxygenation, speed, temperature and $CO_2$ were kept consistently constant for ten days. In certain instances, cancer stem-like cells were cultured in the HFB and exposed for 2 to 6 hours with ozone ($O_3$) levels at levels of 0.08 to 0.40 PPM to cause a fluctuation in the cellular redox environment (redox cycle). Ozone was generated with two OREC Model OZONEV1-O ozonizers (Ozone Research and Equipment Corp., Phoenix, Ariz.), with compressed air used as a source of oxygen, and the concentration of ozone within the chambers was monitored throughout the exposure with three Dasibi 1003 AH ambient-air ozone monitors (Dasibi Environmental Corp., Glendale, Calif.). Cells were then counted and $1 \times 10^6$ cells were placed in the rotating vessel set at 25 rpm with airflow set at 20% for 14 days. Cells were then removed and counted again using trypan blue exclusion to determine cellular viability and cell number and plated in 96 wells for chemosensitivity testing. The cells were also reacted with florescent antibodies for phenotypic characterization.

MACS Sorting. Up to $1 \times 10^7$ cells were sorted by a magnetic-activated cell sorting (MACS) system, which consists of magnetic beads conjugated to an antibody against CD133 (Miltenyi, Auburn, Calif.). In brief, cells were harvested using 0.25% trypsin, pelleted and labeled with CD133/1 biotin and CD133/2-PE. Cells were washed and labeled with anti-biotin magnetic beads, and then passed through a magnetic column where CD133(+) cells were retained, while unlabeled cells passed through the column. The CD133(+) retained cells were eluted from the columns after removal from the magnet. Positive and negative cells were then analyzed by FACS for purity.

Flow Cytometry Studies. Cells were analyzed by antigenic criteria using anti-CD34 (Milteny Biotech, Auburn, Calif.), -CD38 (Milteny Biotech, Auburn, Calif.), -CD44 (BD Bioscience, Sparks, Md.), -CD117 (Milteny Biotech, Auburn, Calif.), -CD133/2 (prominin1) (Milteny Biotech, Auburn, Calif.), -OCT3/4 (BD Bioscience, Sparks, Md.), and -Nanog (BD Bioscience, Sparks, Md.). Briefly, cells were detached using 0.02% EDTA in PBS and pelleted (10 min at 1,000 rpm), washed in 0.1% BSA in 1×PBS at 4° C. and incubated in a solution of 1 mg antibody +9 mL 0.1% BSA in 1×PBS. Cells were washed in the same solution once and were analyzed using a C6 Accuri flow cytometer (BD Biosciences, San Jose, Calif.). Data was analyzed using the FlowJo cell cycle analysis program (BD Biosciences, San Jose, Calif.).

Chemosensitivity assay. Sensitivity and resistance to chemotherapy was assessed using an MTT assay on $1 \times 10^3$ cells plated in 5 replicas into 96-well plates. Briefly, equal number of bulk of tumor cells grown in monolayer and cancer stem-like cells CD133(+) three-dimensionally grown in the bioreactor, were plated separately in 96-well dishes and incubated at 37° C. for 24-hours. Then the cells were challenged for a 1-hour pulse with a panel of anticancer drugs as indicated by the oncologist. Each anticancer drug was tested in a range of doses including the clinically relevant dose. An MTT assay was performed 24-hours following chemotherapy treatment to assess cell viability as previously described. A dose response chart was developed in which samples were scored as responsive (60-100% cell kill), moderately responsive (40-60% cell kill), low to moderate responsive (20-40% cell kill), low responsive (10-20% cell kill), and non-responsive (0-10% cell kill).

Tumorigenic Assay in Nude Mice. $1 \times 10^3$ ependymoma cells were injected subcutaneously in 5 athymic, immune deficient nude mice (FOXN1 mutant) group. Briefly, equal number of bulk of tumor cells grown in monolayer, cancer stem-like cells CD133(+) three-dimensionally grown in the bioreactor, and MACSorted cancer stem-like cells CD133(+) were injected in the flank of nude mice and compared to the growth of CD133 negative cells for 35 days.

Statistical Analysis. Statistical analysis was performed using the IBM SPSS statistical software. The results for each variant in the different experimental designs represent an average of 3 different experiments. The data of 5 measurements were averaged; the coefficient of variation among these values never exceeded 10%. Mean values and standard errors were calculated for each point from the pooled normalized to control data. Statistical analysis of the significance of the results was performed with a 1-way ANOVA. p values of less than 0.05 were considered statistically significant.

Example 1

Selection of Chemotherapeutic Agent and in Subject with Intradural, Extramedullary Anaplastic Recurring Spinal Ependymoma, WHO Grade III Intradural extramedullary ependymomas are rare, and predominately occur in women in the 5th decade of life. The tumors present with pain, paresthesia, and paraparesis, and account for 60% of all intramedullary tumors with 50% of them arising from the filum terminale. From a review of the literature, there have recently been 19 reported cases of primary intradural and extramedullary spinal ependymomas in patients ranging from 24 to 69 years old. Importantly, the clinical condition of the patients temporarily improved in 11 patients, remained stable in 2, and worsened (recurrence or progression) in 6 patients who underwent a combination of surgery, radiation and chemotherapy treatments.

In light of these varying outcomes, it has been observed that, in several types of human cancer, only a subset of cancer cells within each tumor is capable of initiating tumor growth in animal xenograft models. This pool of cancer cells is operationally defined, in some instances, as the cancer stem-like cell subset. Unlike bulk of tumor cells, cancer stem-like cells resist chemotherapy, thereby causing relapse of the disease. In this regard, experiments were undertaken to identify and develop a chemotherapy sensitivity assay, which measures the cytotoxic index in cancer stem-like cells, as well as in the bulk of tumor cells following chemotherapy.

Figure 1B:

To develop the assay, a subject was first identified from which to obtain a suitable cancer cell sample. Briefly, a 17-year-old male subject was identified that had had magnetic resonance imaging (MRI) images taken of his cervical spine, which showed the presence of an abnormal enhancing mass, which extended from mid C5 to inferior C7 (4.5 in length× 1.0×2.0 in cephalocaudal and anteroposterior dimension) that caused cord compression (FIG. 1A). Further MRI images of his thoracic spine showed an enhancing lesion at T2-3 (1.5 in length×0.6×0.6 cm in anteroposterior and transverse dimension) with several other smaller nodular masses, best seen on the T2 weighted sequence, which extended throughout the thoracic level to T11 (FIG. 1B).

Figure 1C:
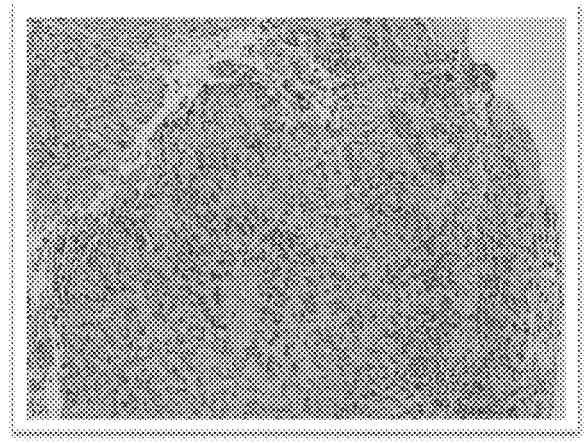

The subject subsequently had a laminectomy in at C5, C6, and C7 with partial resection of the tumor under microscope using microsurgical techniques. Following surgery, the patient was treated with radiation and Temozolomide. Morphological analysis of the histology sections stained with Hematoxylin & Eosin showed an overall predominant dense cellular component, with primitive and pleiomorphic nuclei, increased mitotic rate and apoptosis, and foci with microvascular proliferation, as shown in FIG. 1C. The presence of well formed, obvious perivascular pseudorosettes (with vasocentric pattern, perivascular nuclear-free zones, and classic thin glial processes radiating to/from the vessel wall) were found supportive of the diagnosis of intradural, extramedullary anaplastic diffuse spinal ependymoma, WHO grade III.

Sections of the tumor were then evaluated by immunoperoxidase techniques with appropriate staining control sections. The tumor showed positive staining with antibodies to neuron specific enolase, vimentin, S-100, and GFAP. Weak staining occurred with the antibodies against actin. Focal staining occurred with antibodies to epithelial membrane antigen, cytokeratin AE1/AE3, and synaptophysin. The tumor was negative for leukocyte common antigen, desmin, and myogenin. In addition, a section stained with PAS showed a focal PAS-positive fibrillar material. Sections and tumor block were also sent to a biopathology center of a children's oncology group where two neuropathologists independently reviewed the case and confirmed the diagnosis of anaplastic ependymoma, WHO grade III.

Figure 2A:
FIGS. 2A-2D are MRI images of a cervical spine showing recurrence in the surgical area (FIG. 2A), the thoracic spine showing progression of the main lesion measuring 23.9 mm and the appearance of several other smaller lesions (FIG. 2B), and the cervical (FIG. 2C) and thoracic (FIG. 2D) spine showing tumor regression.

Following the diagnosis, the subject received complex chemotherapy over the next several months in multiple rounds with Cytoxan, thalidomide, Celebrex followed by etoposide, thalidomide and Celebrex. Chemotherapy was stopped several months after the initial treatment due to a tumor regrowth at T7-T8 for which the subject underwent Cyberknife treatment. The subject then had debulking surgery, but approximately 6-months later, he had progressive numbness in his legs along with back pain with MRI showing recurrence in the surgical area (FIG. 2A) as well as the lumbar spine. He was then started back on temozolomide, but had no response to treatment.

Figure 2B:

Four months later, the subject underwent a thoracic laminectomy and resection of the intradural intramedullary tumor due to the progression of disease. He had severe spinal compression and began having weakness in his legs and he was put in an experimental program, but had no response. The patient then had another debulking surgery and also received oxaliplatin and etoposide treatment, but progressed again (FIG. 2B).

To assess whether more appropriate treatments could be selected for the subject, a cancer cell sample was then provided from the subject for culturing by taking a sterile biopsy of the subject's tumor during the debulking surgery. A single-cell suspension was then prepared from the ependymoma biopsy by first placing the biopsy in RPMI-1640 sterile media. Then, using the GENTLEMACS™ magnetic-activated cell sorting Dissociator (Miltenyi, Auburn, Calif.) and C Tubes, a standardized, semi-automated protocol based on a combination of mechanical tissue disruption and incubation with a 50% solution 0.025% trypsin and Accutase (Innovative Cell Technologies, San Diego, Calif.) was performed.

The single-cell ependymoma suspension was then plated in RPMI-1640 in the presence of 5% heat inactivated fetal bovine serum, streptomycin and penicillin and cells were cultured as a monolayer for 15 days. Cells were immunophenotyped by flow cytometer using anti-CD34 (Milteny Biotech, Auburn, Calif.), -CD38 (Milteny Biotech, Auburn, Calif.), -CD44 (BD Bioscience, Sparks, Md.), -CD117 (Milteny Biotech, Auburn, Calif.), -CD133/2 (prominin1) (Milteny Biotech, Auburn, Calif.), -OCT3/4 (BD Bioscience, Sparks, Md.), and -Nanog (BD Bioscience, Sparks, Md.). Briefly, cells were detached using 0.02% EDTA in PBS and pelleted (10 min at 1,000 rpm), washed in 0.1% BSA in 1×PBS at 4° C. and incubated in a solution of 1 mg antibody +9 mL 0.1% BSA in 1×PBS. Cells were washed in the same solution once and were analyzed using a C6 Accuri flow cytometer (BD Biosciences, San Jose, Calif.). Data was analyzed using the flow-Jo cell cycle analysis program (BD Biosciences, San Jose, Calif.).

Figure 3A:
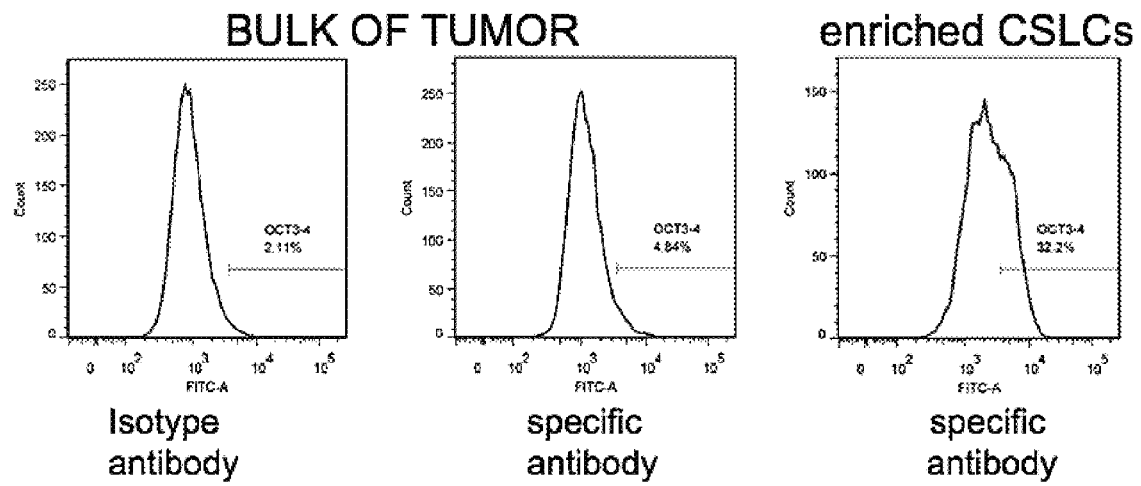
FIGS. 3A-3H are graphs and images showing the characterization of a primary ependymoma cell culture (Bulk of Tumor) and an enriched cancer stem-like cell culture (enriched CSLC), including: graphs showing the immunophenotyping of the cultured cells using an OCT3/4 antibody (FIG. 3A), a Nanog antibody (FIG. 3B), a CD133 antibody (FIG. 3C), a CD117 antibody (FIG. 3D), a CD44 antibody (FIG. 3E), and double labeling with CD34 and CD38 antibodies (FIG. 3F); a contrast phase image of a cluster of enriched CSLCs following 7-days of culture in the hydrofocusing bioreactor (FIG. 3G); and an image of immunodeficient nude mice (nu/nu) subsequent to injected with $1\times10^3$ MacSorted CD133(+) cells (upper mouse) or CD133(+) ependymoma cells grown in the hydrofocusing bioreactor (lower mouse) showing tumor formation after 35 days (FIG. 3H)
Figure 3B:
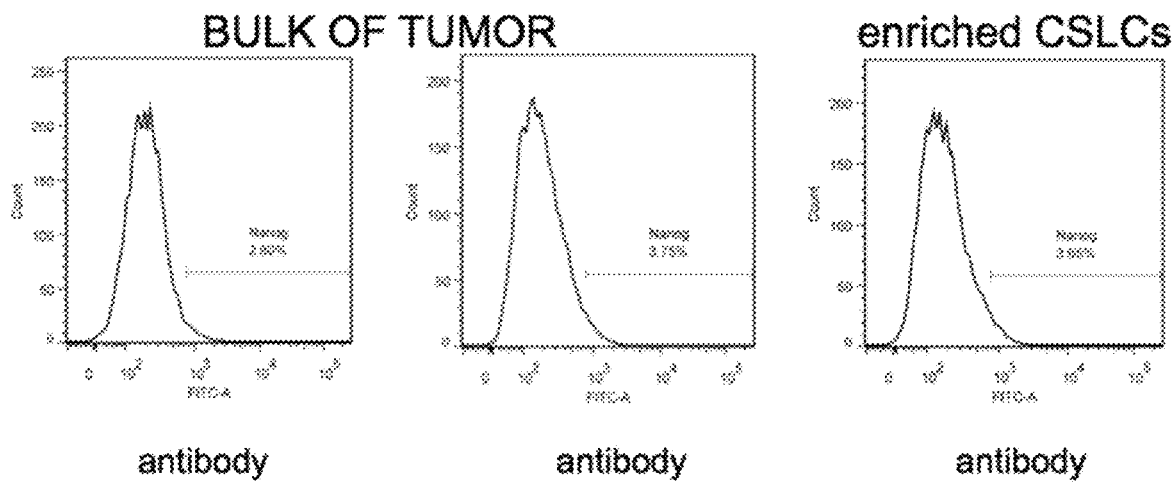
Figure 3C:
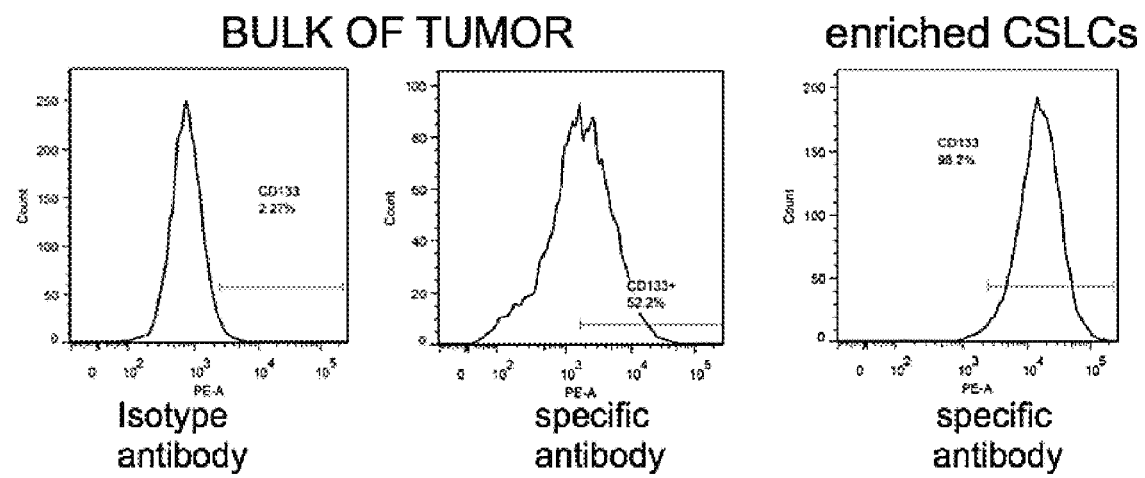
Figure 3D:
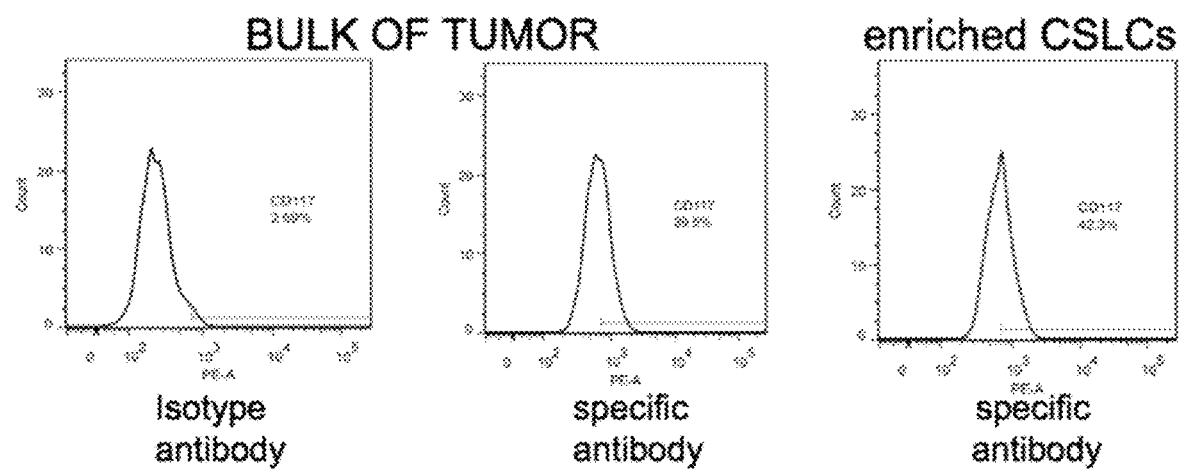
Figure 3E:
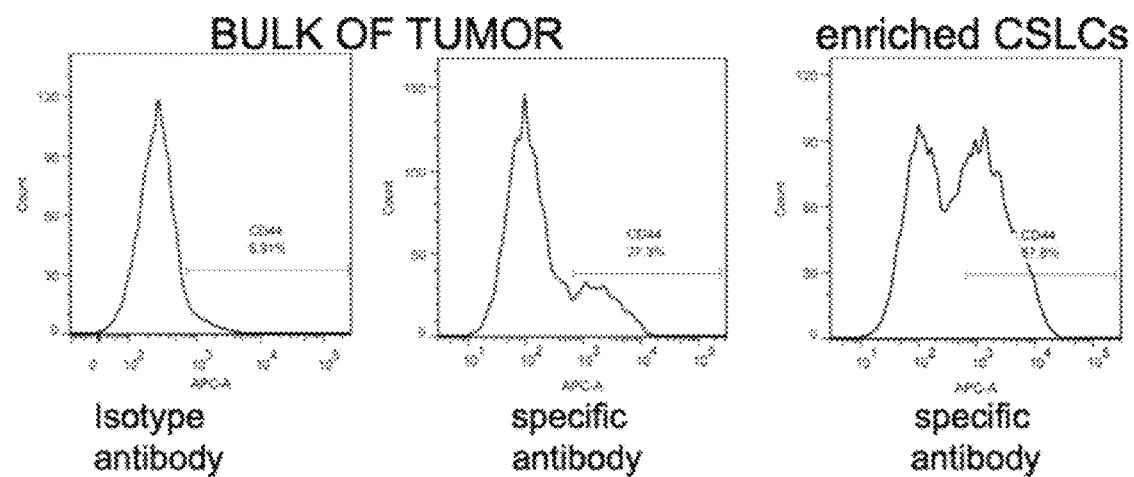
Figure 3F:
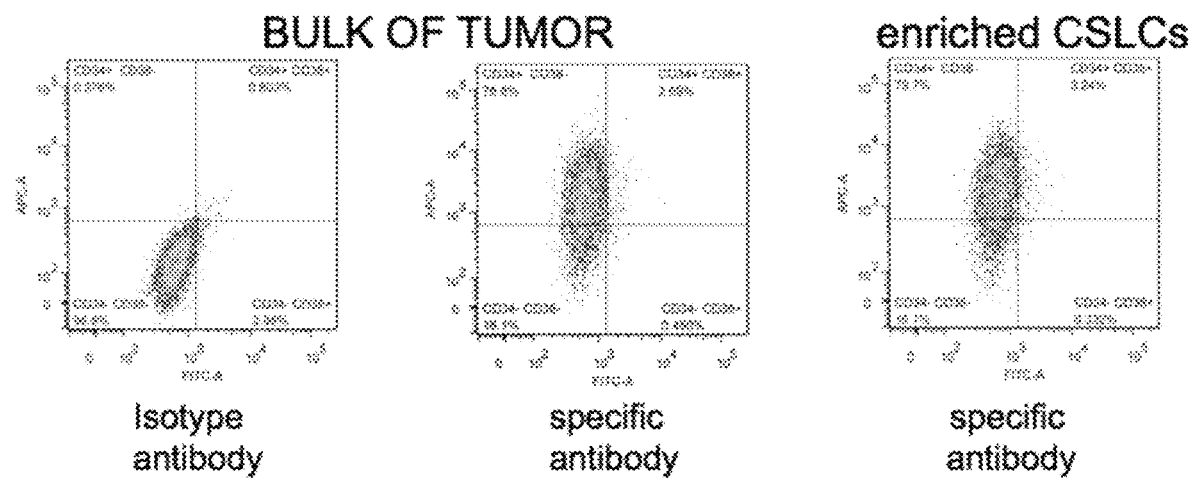

The ependymoma cells were found positive to OCT3/4 (2.73%), Nanog (0.95%), CD133 (49.93%), CD117 (36.81%), and CD44 (20.39%) when compared to an isotype control antibody, as shown in FIGS. 3A-3E and FIG. 4. A double staining of CD34 and CD38 showed the presence of 1.88% of the cells CD34+/CD38+, and 78.4% CD34+/CD38− cells, as shown in FIG. 3F.

Figure 3G:
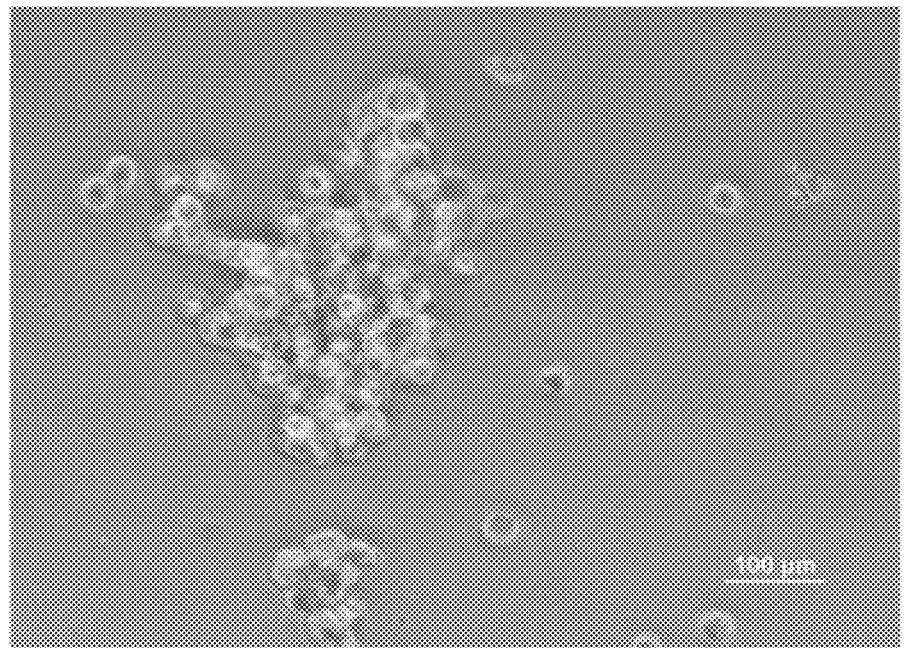

To then expand the immature cancer stem-like cell population of CD 133+ cells present within the ependymoma primary culture, the ependymoma cells were grown in a rotating vessel, as previously described [8]. Briefly, $1 \times 10^6$ of the ependymoma cells from a monolayer culture were grown for ten days using a Hydrodynamic Focusing Bioreactor (HFB) (Celdyne, Houston, Tex.) at 25 rpm with airflow set at 20%, and culture media, oxygenation, speed, temperature and $CO_2$ were kept consistently constant for ten day period. Following the ten day period, cells were then removed and counted again from the HFB, and trypan blue exclusion was used to determine cellular viability and cell number. The cells were also reacted with florescent antibodies for phenotypic characterization. It was observed that as a result of the ten day culture in the HFB, the ependymoma cells formed cell clusters (FIG. 3G), were expanded 14.7 fold, and appeared to be 95.93% CD133 positive, as also shown in FIG. 3C and Table 1 below.

TABLE 1

Selective Enhancement of CD133+ Cancer Stem-like Cells Using a Hydrodynamic Focusing Bioreactor.

|  | CD133+ cells | CD133− cells |
| --- | --- | --- |
| Day 0 | 255,000 | 245,000 |
| Day 7 | 3,748,500 | 159,036 |
| Fold | 14.7 | −1.54 |

To verify the tumor initiating capacity of the CD133+ cells, CD133+ were injected into mice. To first obtain the CD133+ cells, up to 1×10⁷ cells were sorted by a magnetic-activated cell sorting (MACS) system, which consists of magnetic beads conjugated to an antibody against CD133 (Miltenyi, Auburn, Calif.). Cells were harvested using 0.25% trypsin, pelleted, and labeled with CD133/1 biotin and CD133/2-PE. Cells were washed and labeled with anti-biotin magnetic beads, and then passed through a magnetic column where CD133(+) cells were retained, while unlabeled cells passed through the column. The CD133(+) retained cells were eluted from the columns after removal from the magnet. The purity of the positive and negative cells was then analyzed by fluorescence-activated cell sorting.

Figure 3H:
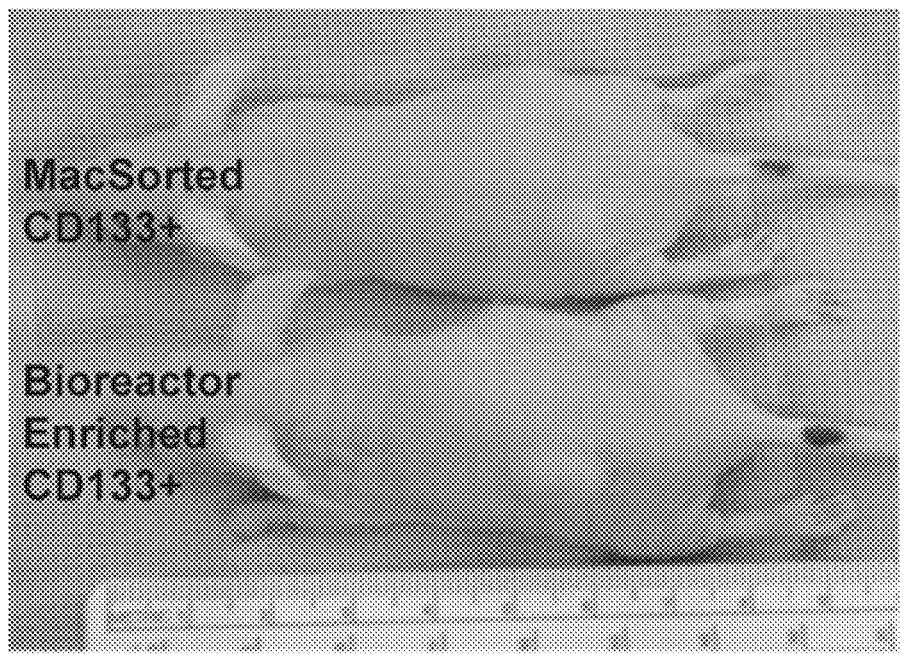
Figure 4:
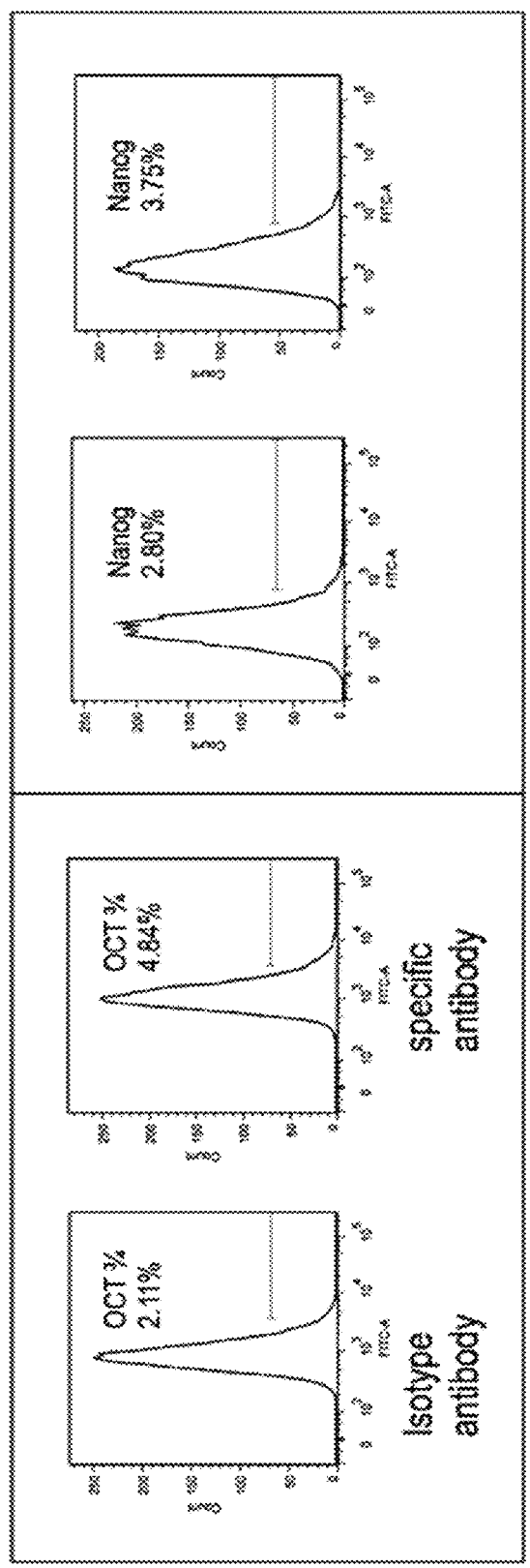
FIG. 4 includes graphs showing the immunophenotyping of cancer cells using a CD133 antibody, a CD34 antibody, a CD 38 antibody, a CD44 antibody, a CD117 antibody, an OCT3/4 antibody, and a Nanog antibody, and further illustrating the percent of positive cells.
Figure 4:
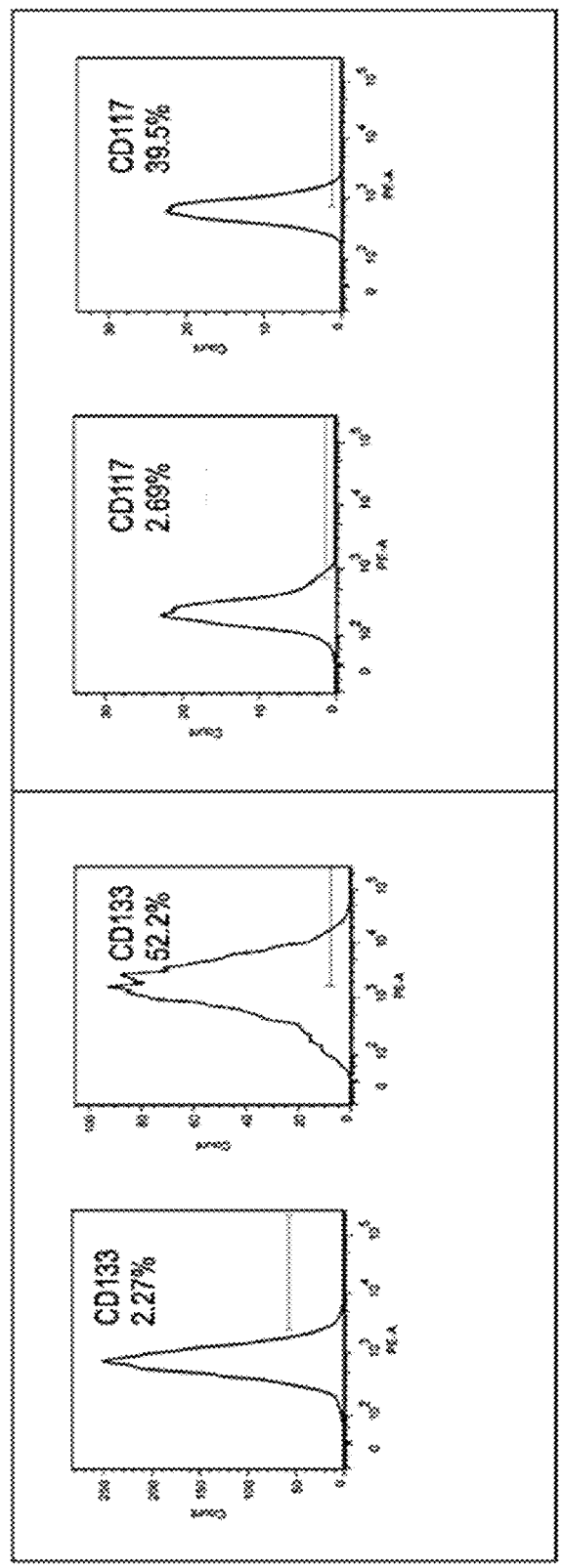
Figure 4:
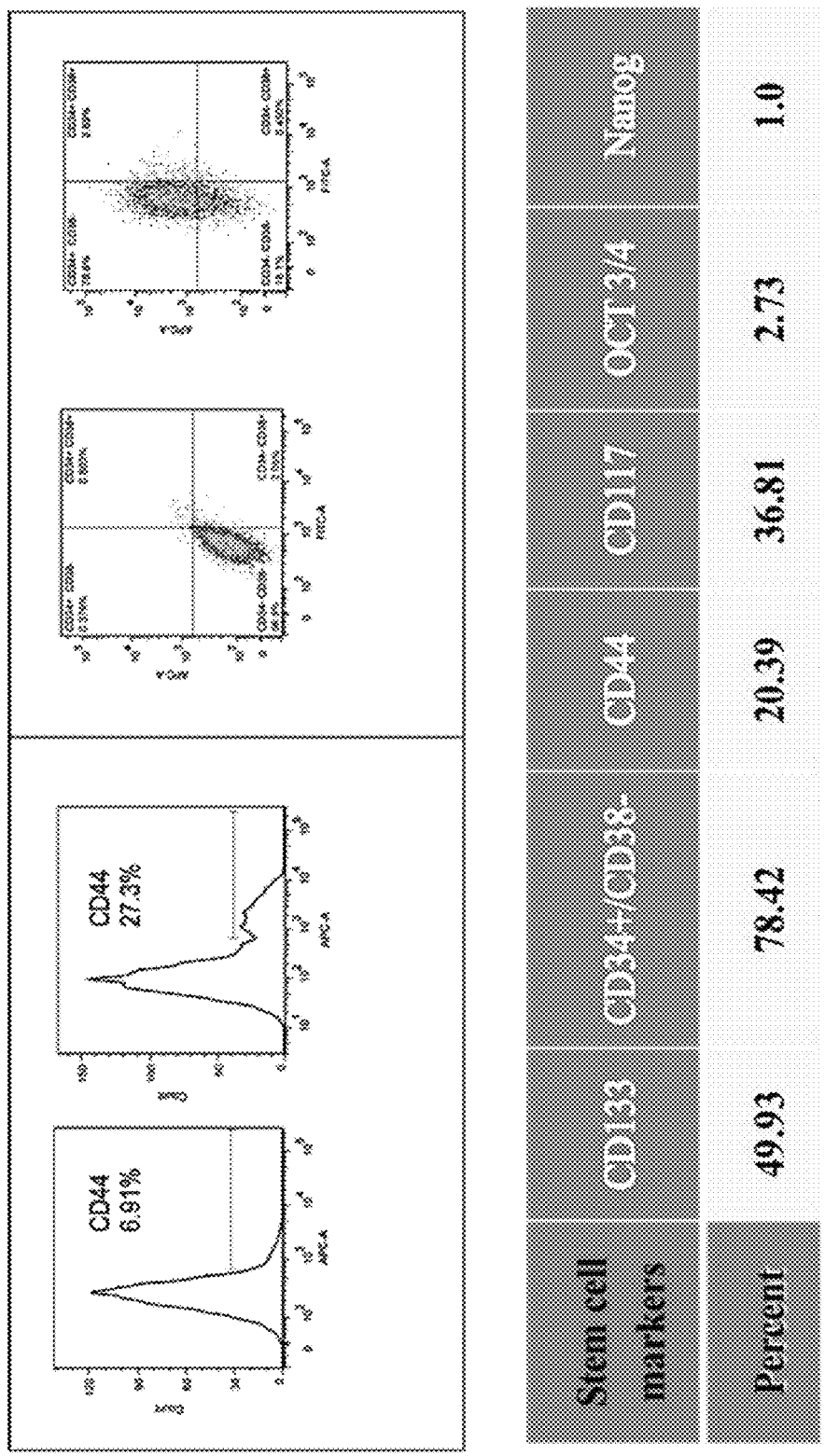

Upon sorting the cells, 1×10³ CD133(+) cells that were MACS sorted, CD133(+) cells grown in the HFB, and bulk cancer cells that were grown as a monolayer were injected into the flanks of 5 athymic, immune deficient nude mice (FOXN1 mutant). The growth of the CD133(+) cells was compared to the growth of CD133 negative cells. It was observed that both the MACS sorted CD133(+) cells and the CD133(+) from the HFB grew in all the 5 mice injected and formed a palpable tumor within 35 days, as shown in FIG. 3H.

To assess the efficacy of various chemotherapeutic agents on the cancer cell sample collected in Example 2, an MTT assay was performed on 1×10⁵ cells plated in 5 replicas into 96-well plates. Briefly, equal number of the bulk cancer cells grown in a monolayer and the CD133(+) cancer stem-like cells grown in the HFB were plated separately in 96-well dishes and incubated at 37° C. for 24-hours. Then, each of the cell cultures were challenged for a 1-hour pulse with various chemotherapeutic agents, including cisplatin, oxaliplatin, arabinoside-C, VP-16, busulfan, methotrexate, CPT-11, and doxorubicin. Each chemotherapeutic agent was tested in a range of doses including their respective clinically relevant doses.

Figure 5:
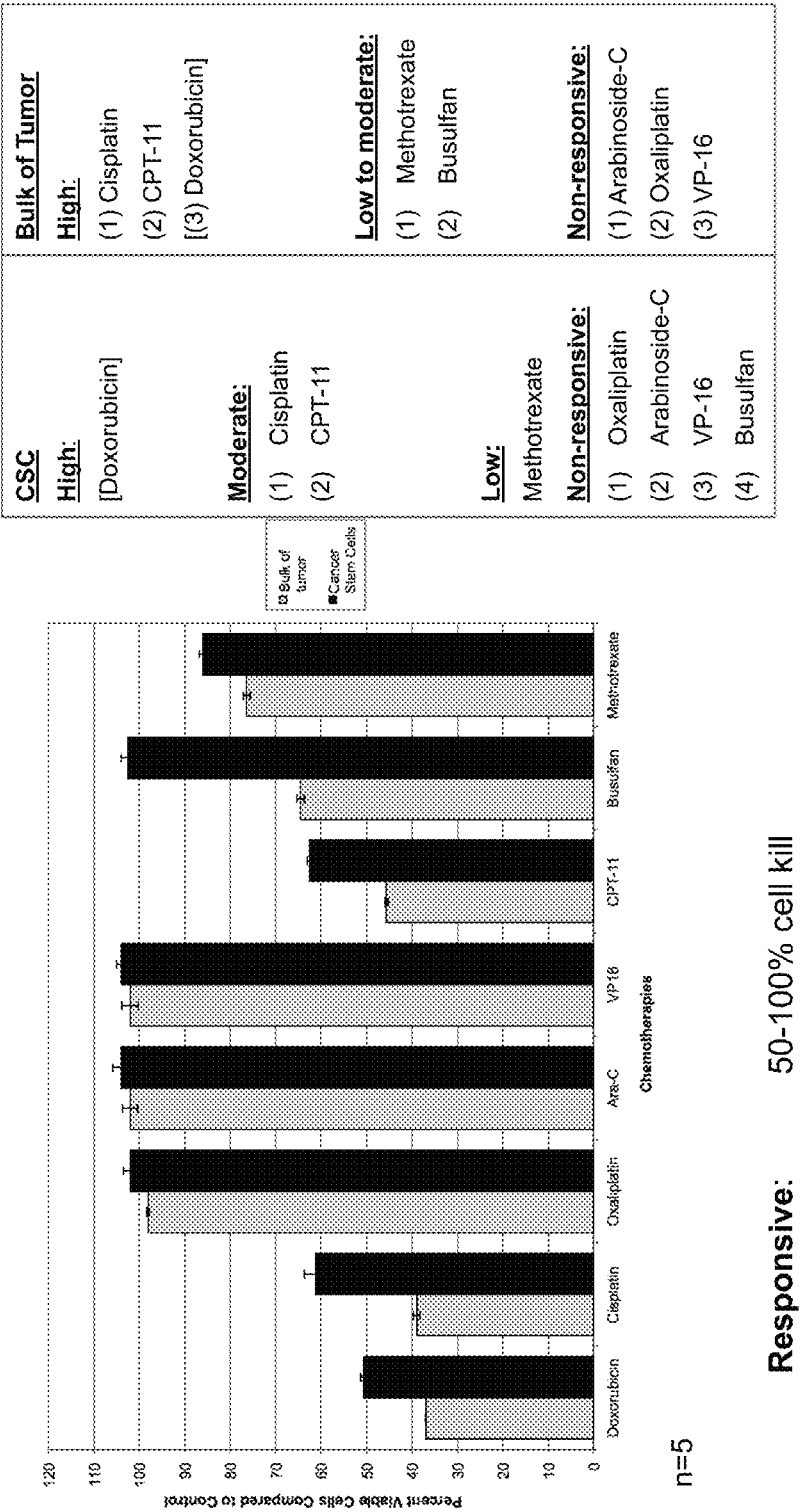
FIG. 5 is a graph and corresponding chart of an assay used to assess the sensitivity of bulk cancer cells (gray) or cancer stem-like cells (black) to chemotherapy, where the bulk cancer cells and cancer stem-like cells were obtained from a subject diagnosed with anaplastic ependymoma, where $1\times10^3$ bulk tumor cells or CSLCs were plated in 5 replicas into 96-well plates and were challenged for a 1-hour pulse with a panel of chemotherapeutic agents, where an MTT assay was performed 24-hours following chemotherapy treatments to assess cell viability, and where the dose response chart shows the scoring of samples as responsive (60-100% cell kill), moderately responsive (40-60% cell kill), low to moderate responsive (20-40% cell kill), low responsive (10-20% cell kill), and non-responsive (0-10% cell kill)

The MTT assay was then performed 24-hours following the chemotherapy treatment to assess cell viability [13]. A dose response chart was developed in which samples were scored as responsive (60-100% cell kill), moderately responsive (40-60% cell kill), low to moderate responsive (20-40% cell kill), low responsive (10-20% cell kill), and non-responsive (0-10% cell kill). This assessment was independently performed for both the bulk cancer cells and the cancer stem-like cells of the ependymoma cancer cell sample. Upon analysis of the results from the MTT assay, it was observed that the ependymoma cells grown in a monolayer, and representing the bulk cancer cells, were sensitive to a single treatment of cisplatin, CPT-11, and doxorubicin. Interestingly, the isolated cancer stem-like cells exhibited moderate chemosensitivity to cisplatin and CPT-11, and were highly sensitive to doxorubicin treatments. On the other hand, both the cancer stem-like cells and the bulk cancer cells were minimally to moderately responsive to methotrexate and busulfan, and were completely not responsive to oxaliplatin, arabinoside-C, and VP-1, as shown in FIG. 5.

Figure 2C:
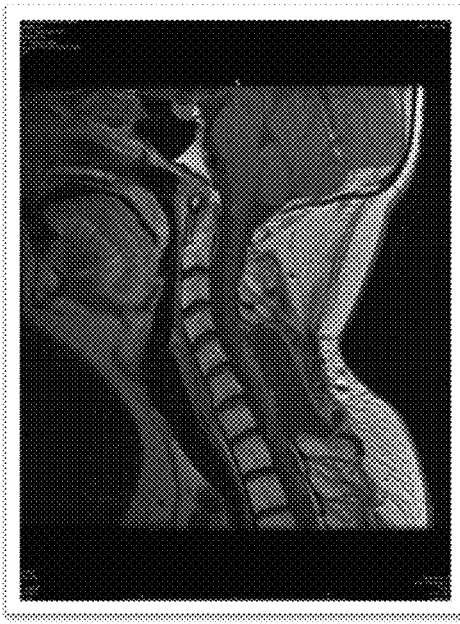
Figure 2D:

In light of the foregoing results, and because the subject of the Examples previously lacked a response to an oxaliplatin and etoposide management, the subject then began being administered bevacizumab and Campotosar (CPT-11), which were given approximately every two weeks for 6 months, but, ultimately, had to be stopped due to systemic toxicity. However, although the patient was suspended from bevacizumab and Camtosar (CPT-11) therapy, he remained free from disease progression for 18 months, as shown in FIGS. 2C and 2D. This 18-month period corresponded to the longest disease progression free period observed for this subject since his initial diagnosis, thus indicating that the foregoing methodology was useful for the selection of a chemotherapeutic agent for treating cancer that is active against both the cancer stem-like cells and the bulk cancer cells found in the cancer.

Figure 6:
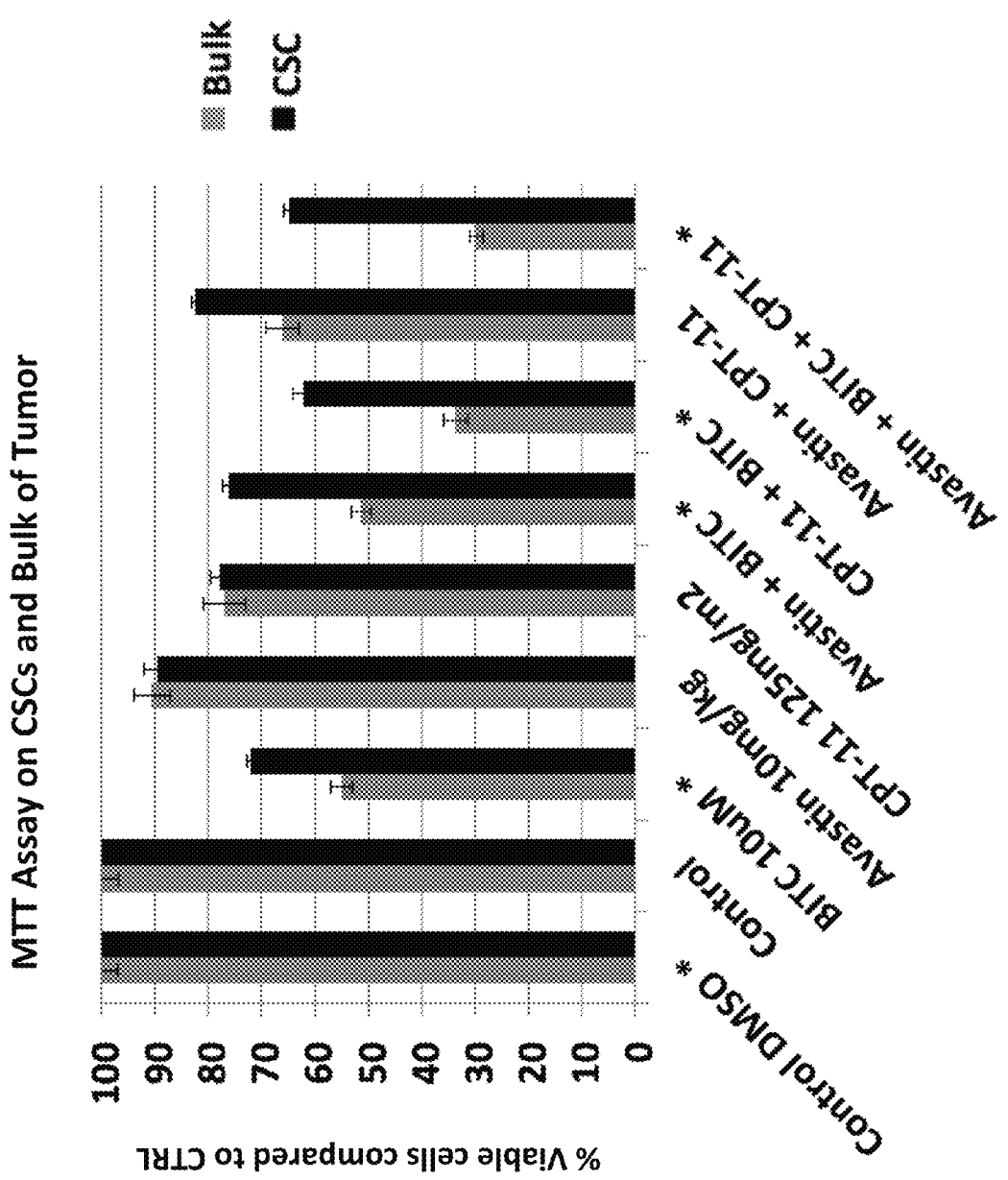
FIG. 6 is a graph showing the results of an MTT assay used to assess cell viability of bulk cancer cells and cancer stem-like cells obtained from a reoccurrence of a tumor in a subject diagnosed with anaplastic ependymoma and exposed to a variety of chemotherapeutic agents.
Figure 7A:
FIGS. 7A-7D include images showing the reoccurrence of a tumor in a subject diagnosed with anaplastic ependymoma (FIGS. 7A-7B) and showing a 60% reduction in the tumor size at 2-months following treatment with a combination therapy of bevacizumab (AVASTIN®, Genentech Inc., San Francisco, CA), irinotecan (CPT-11), and benzyl isothiocyanate (BITC)
Figure 7B:
Figure 7C:
Figure 7D:

Subsequent to the 18-month period in which the ependymoma did not progress, a reoccurrence occurred (FIG. 7A-7B), and a further surgery was performed with a biopsy being taken for chemotherapeutic agent screening via an MTT assay as described herein above. Upon analysis of the results from the MTT assay, it was observed that both the cancer stem-like cells and the bulk cancer cells were sensitive to: benzyl isothiocyanate (BITC); a combination of bevacizumab and BITC; a combination of CPT-11 and BITC; and a combination of bevacizumab (AVASTIN®, Genentech, San Francisco, Calif.), BITC, and CPT-11 (FIG. 6). After reviewing the results in detail, it appeared that the combination of bevacizumab, BITC, and CPT-11 was the most effective in causing a reduction in both the cancer stem-like cells and the bulk cancer cells and, as such, that combination was chosen for administration to the subject. Following treatment with that combination, a 60% reduction in the tumor was further observed (FIGS. 7C-7D).

Example 2

Figure 8:
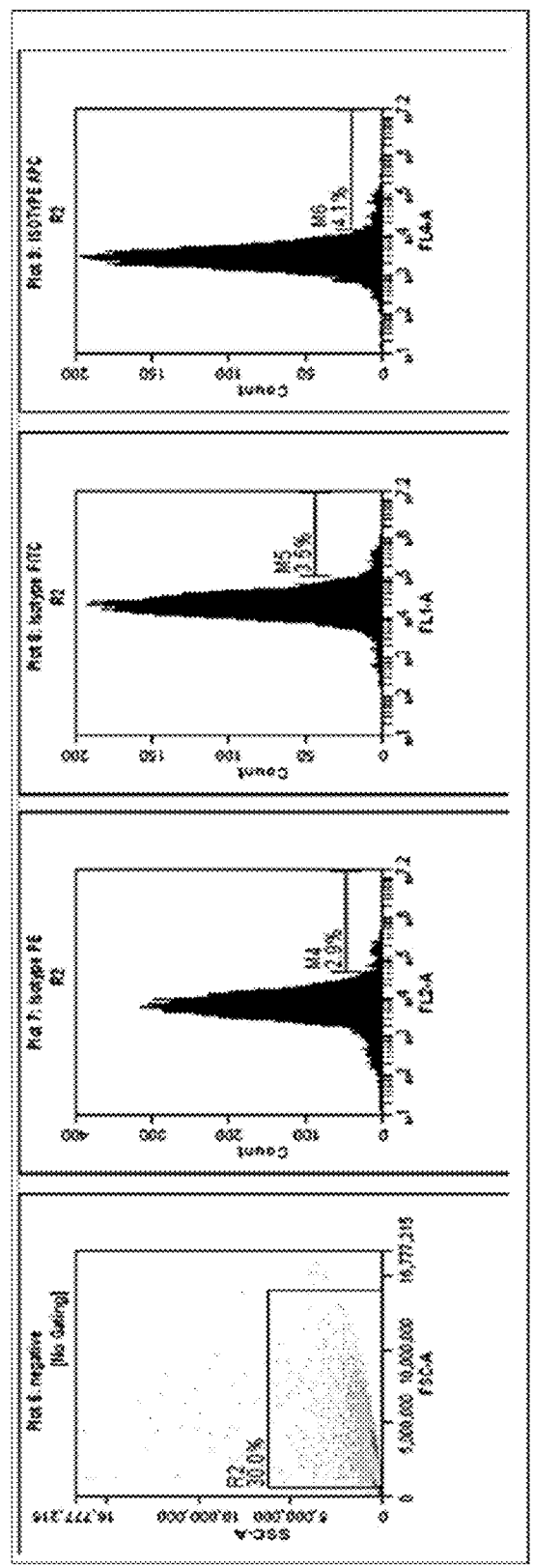
FIG. 8 includes graphs showing the immunophenotyping of cancer cells obtained from an anaplastic ependymoma tumor using a CD133 antibody, a CD34 antibody, a CD38 antibody, a CD44 antibody, a CD117 antibody, an OCT3/4 antibody, and a Nanog antibody, and further illustrating the percent of positive cells.
Figure 8:
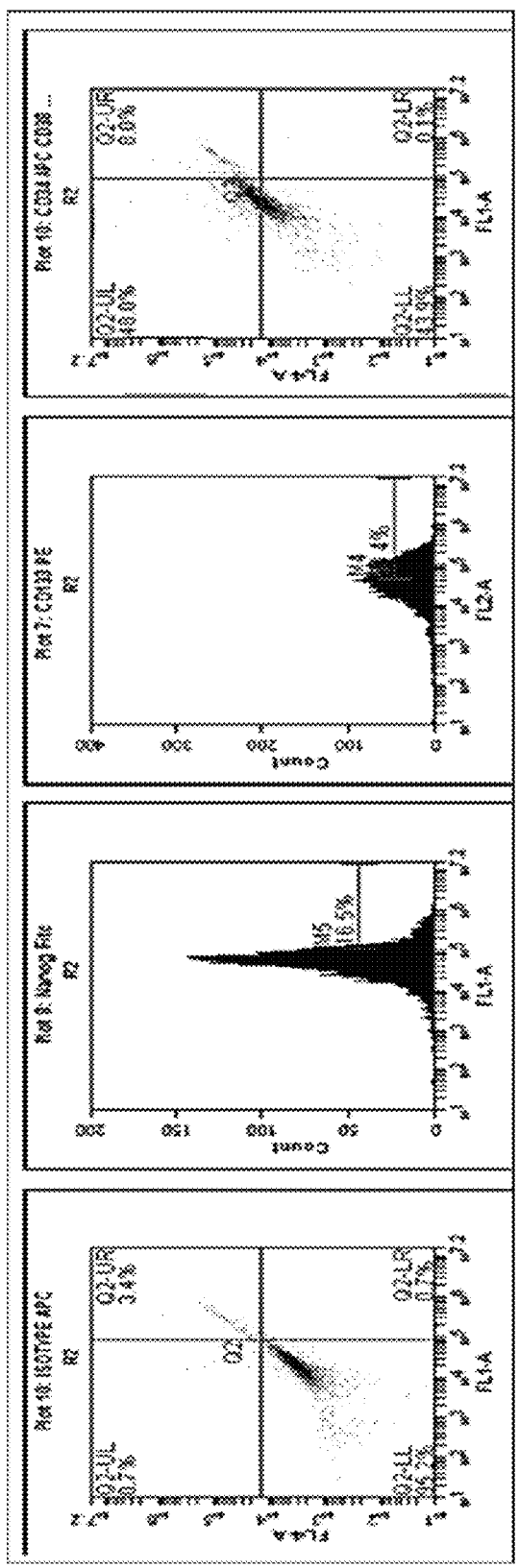
Figure 8:
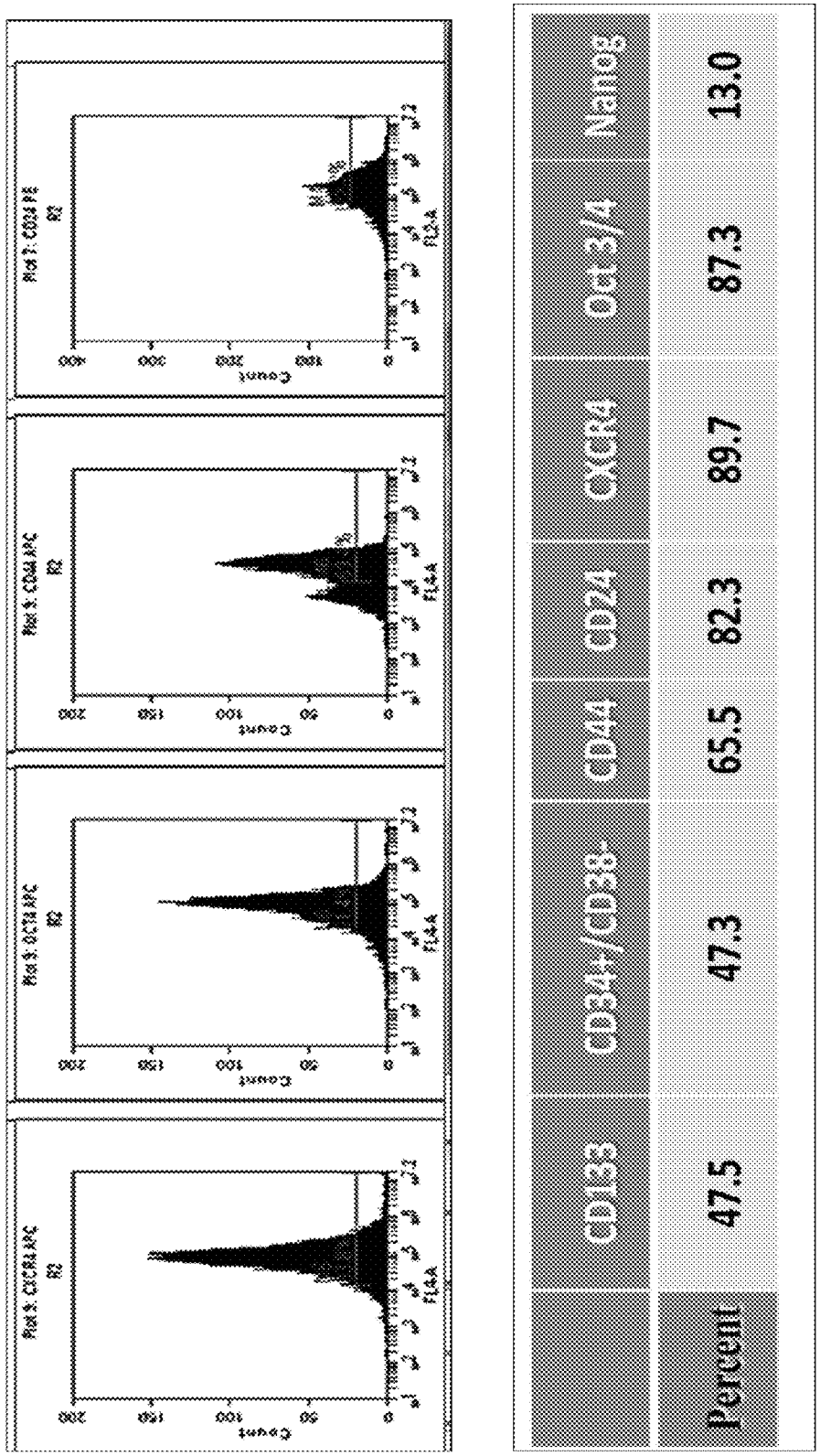

Selection of Chemotherapeutic Agent and Treatment of 5-Month Old Subject with Anaplastic Ependymoma WHO Grade III To further assess the ability of the presently-disclosed methodology to identify chemotherapeutic agents capable of treating both cancer stem-like cells and bulk cancer cells in a subject diagnosed with cancer, a cancer cell sample was obtained from a 5-month old female subject diagnosed with anaplastic ependymoma, WHO grade III. Similar to the experiments described herein above, the cancer cell sample was initially cultured as a suspension and the cancer cells were immunophenotyped by flow cytometer using anti-CD133 (Milteny Biotech, Auburn, Calif.), -CD34 (Milteny Biotech, Auburn, Calif.), -CD38 (Milteny Biotech, Auburn, Calif.), -CD44 (BD Bioscience, Sparks, Md.), -CD24 (Milteny Biotech, Auburn, Calif.), -CXCR4 (Milteny Biotech, Auburn, Calif.), -OCT3/4 (BD Bioscience, Sparks, Md.), and -Nanog (BD Bioscience, Sparks, Md.). The ependymoma cells were found positive to CD133 (47.5%) CD44 (65.5%), CD24 (82.3%), CXCR4 (89.7%), OCT3/4 (87.3%), and Nanog (13.0%) when compared to an isotype control antibody, as shown in FIG. 8. A double staining of CD34 and CD38 showed the presence of 47.3% CD34+/CD38− cells, as also shown in FIG. 8.

Figure 9:
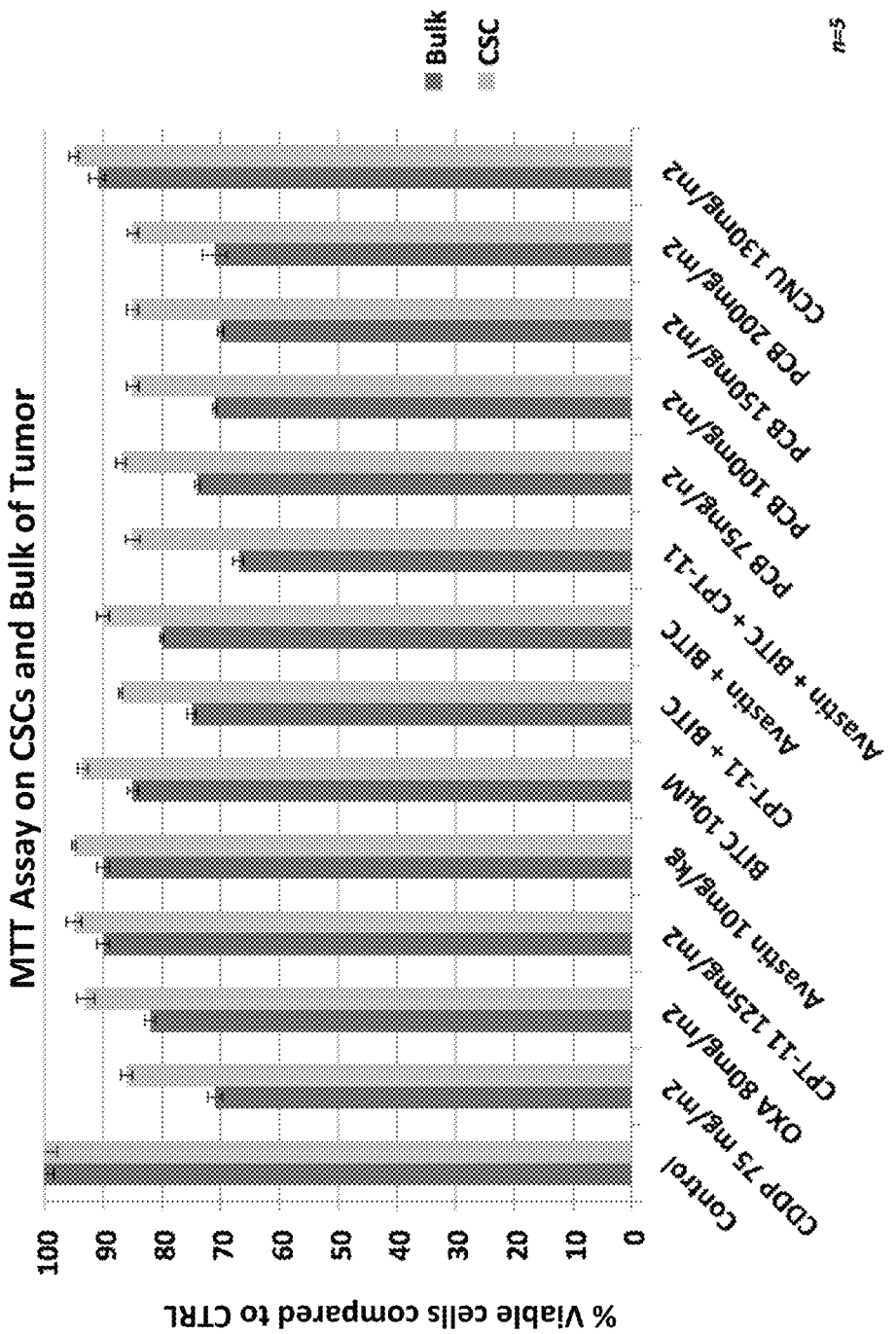
FIG. 9 is a graph showing the results of an MTT assay used to assess cell viability of bulk cancer cells and cancer stem-like cells obtained from an anaplastic ependymoma tumor and exposed to various chemotherapeutic agents.

Then, to then expand the immature cancer stem-like cell population of CD133+ cells present within the ependymoma primary culture, the ependymoma cells were grown in a rotating vessel, as describe herein above and as previously described [8]. To assess the efficacy of various chemotherapeutic agents on the cancer cell sample, an MTT assay was the performed as also described herein. Upon analysis of the results from the MTT assay, it was observed that both the cancer stem-like cells and the bulk cancer cells were only moderately sensitive (30% cell kill) to only cisplatin (CDDP) and procarbazine (PCB) and were not sensitive to oxaliplatin (OXA), CPT-11, bevacizumab, BITC, lomustine (CCNU), and their combinations (FIG. 9). After 6 cycles of vincristine, carboplatin, cyclophosphamide, etoposide, and cisplatin, however, the tumor in the subject rapidly progressed and proton beam therapy was ultimately recommended.

Example 3

Figure 10:
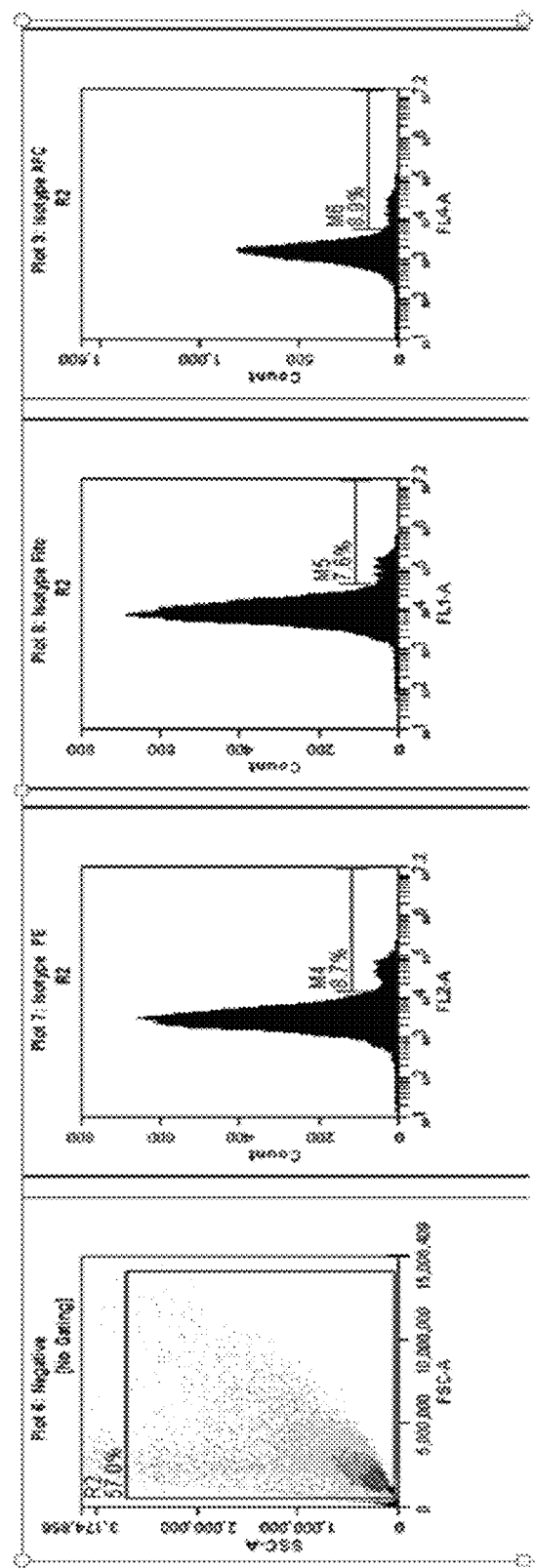
FIG. 10 includes graphs showing the immunophenotyping of cancer cells obtained from an IDH-1 negative glioblastoma tumor using a CD133 antibody, a CD34 antibody, a CD38 antibody, a CD44 antibody, a CD117 antibody, an OCT3/4 antibody, and a Nanog antibody, and further illustrating the percent of positive cells.
Figure 10:
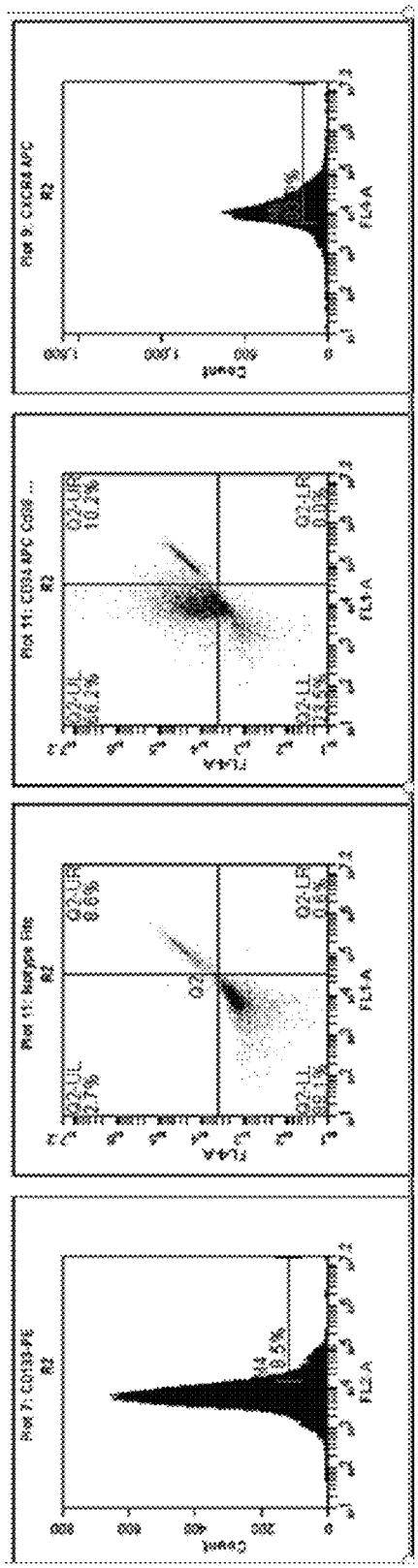
Figure 10:
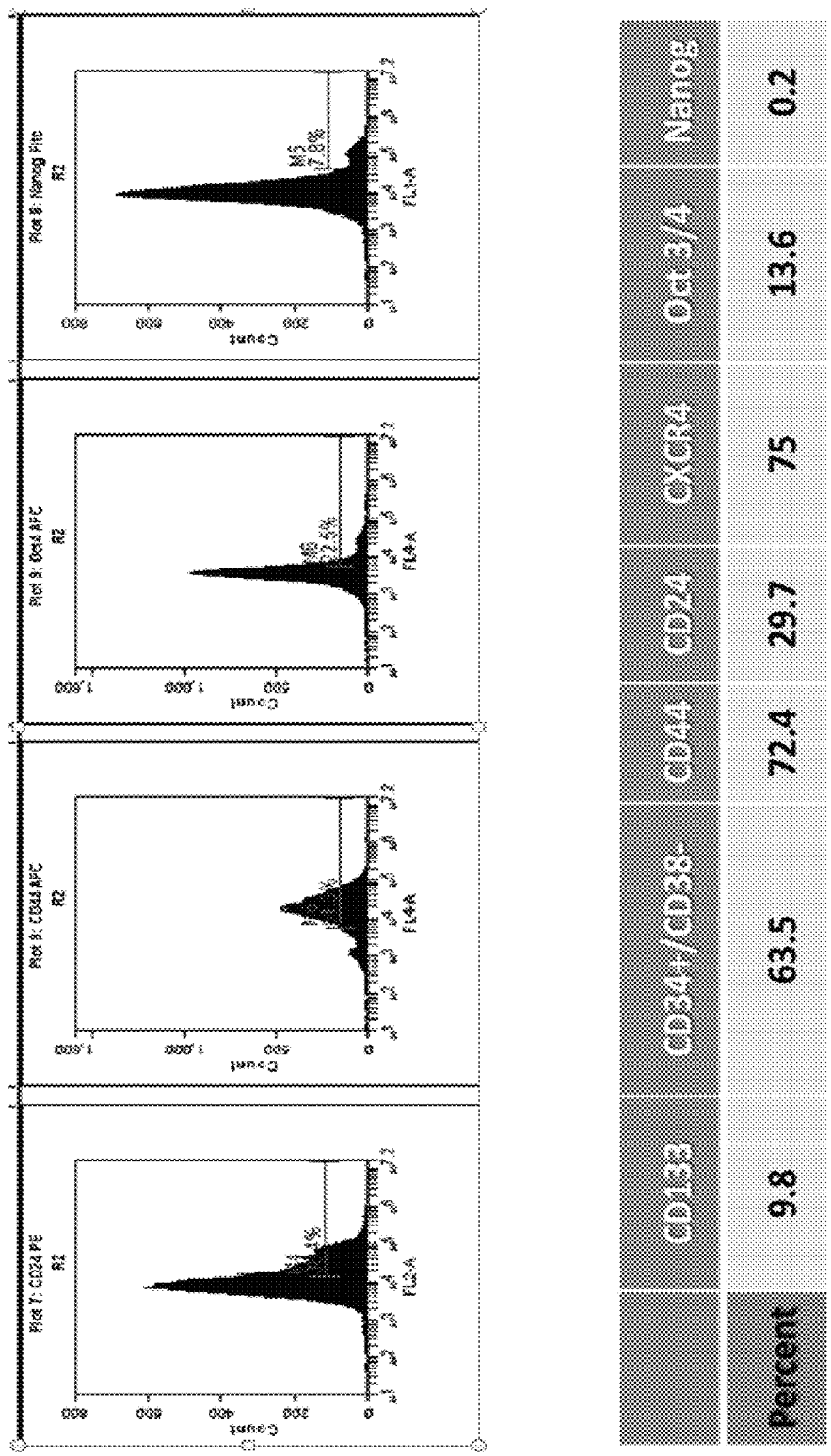

Selection of Chemotherapeutic Agent and in Subject with IDH-1 Negative Glioblastoma, WHO Grade IV A cancer cell sample was also obtained from a subject diagnosed with isocitrate dehydrogenase-1 negative glioblastoma to further assess the ability of the presently-disclosed methodology. Again, similar to the experiments described herein above, the glioblastoma cancer cell sample was initially cultured as a suspension and the cancer cells were immunophenotyped by flow cytometer using anti-CD133 (Milteny Biotech, Auburn, Calif.), -CD34 (Milteny Biotech, Auburn, Calif.), -CD38 (Milteny Biotech, Auburn, Calif.), -CD44 (BD Bioscience, Sparks, Md.), -CD24 (Miltenу Biotech, Auburn, Calif.), -CXCR4 (Milteny Biotech, Auburn, Calif.), -OCT3/4 (BD Bioscience, Sparks, Md.), and -Nanog (BD Bioscience, Sparks, Md.). The glioblastoma cells were found positive to CD133 (9.8%) CD44 (72.4%), CD24 (29.7%), CXCR4 (75%), Oct/3;4(13.6%), and Nanog (0.2%) when compared to an isotype control antibody, as shown in FIG. 10. A double staining of CD34 and CD38 showed the presence of 63.5% CD34+/CD38− cells, as also shown in FIG. 10.

Figure 11:
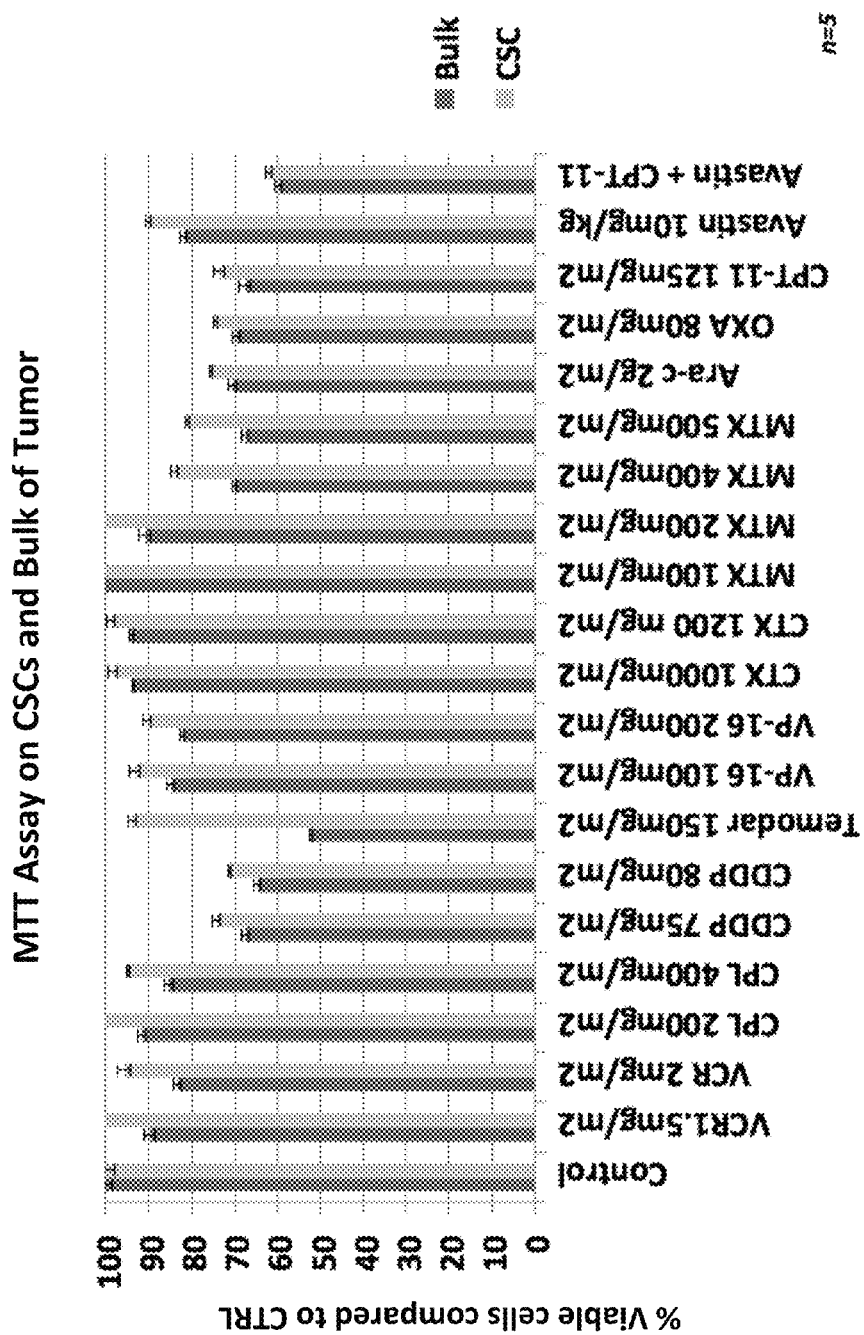
FIG. 11 is a graph showing the results of an MTT assay used to assess cell viability of bulk cancer cells and cancer stem-like cells obtained from an IDH-1 negative glioblastoma tumor and exposed to various chemotherapeutic agents.

Then, to then expand the immature cancer stem-like cell population present within the glioblastoma primary culture, the glioblastoma cells were grown in a rotating vessel, as describe herein above and as previously described [8]. To assess the efficacy of various chemotherapeutic agents on the cancer cell sample, an MTT assay was then performed as also described herein. Upon analysis of the results from the MTT assay, it was observed that the bulk-cancer cells were responsive to temozolomide (TEMODAR®, Merck, Whitehouse Station, N.J.) (50% cell kill), while the cancer stem-like cells were non-responsive to temozolomide at the concentration tested. However, both the cancer stem-like cells and the bulk cancer cells were only intermediately responsive (40% cell kill) to a combination of bevacizumab and CPT-11 (FIG. 11). Nevertheless, the subject was ultimately placed on temozolomide by his treating physician and, after an initial tumor regression, the tumor reoccurred 6 months after the completion of that therapy, possibly due to the non-responsive nature of the cancer stem-like cells at the concentration of temozolomide tested.

Example 4

Figure 12:
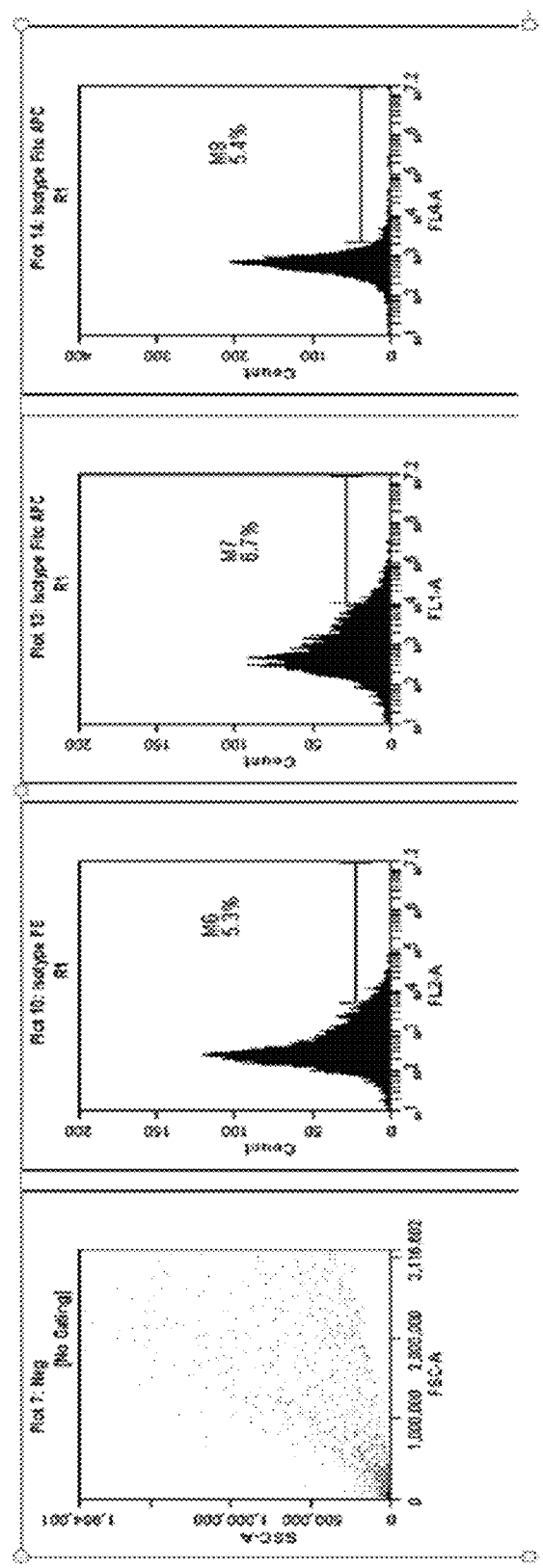
FIG. 12 includes graphs showing the immunophenotyping of cancer cells obtained from another IDH-1 negative glioblastoma tumor using a CD133 antibody, a CD34 antibody, a CD38 antibody, a CD44 antibody, a CD117 antibody, an OCT3/4 antibody, and a Nanog antibody, and further illustrating the percent of positive cells.
Figure 12:
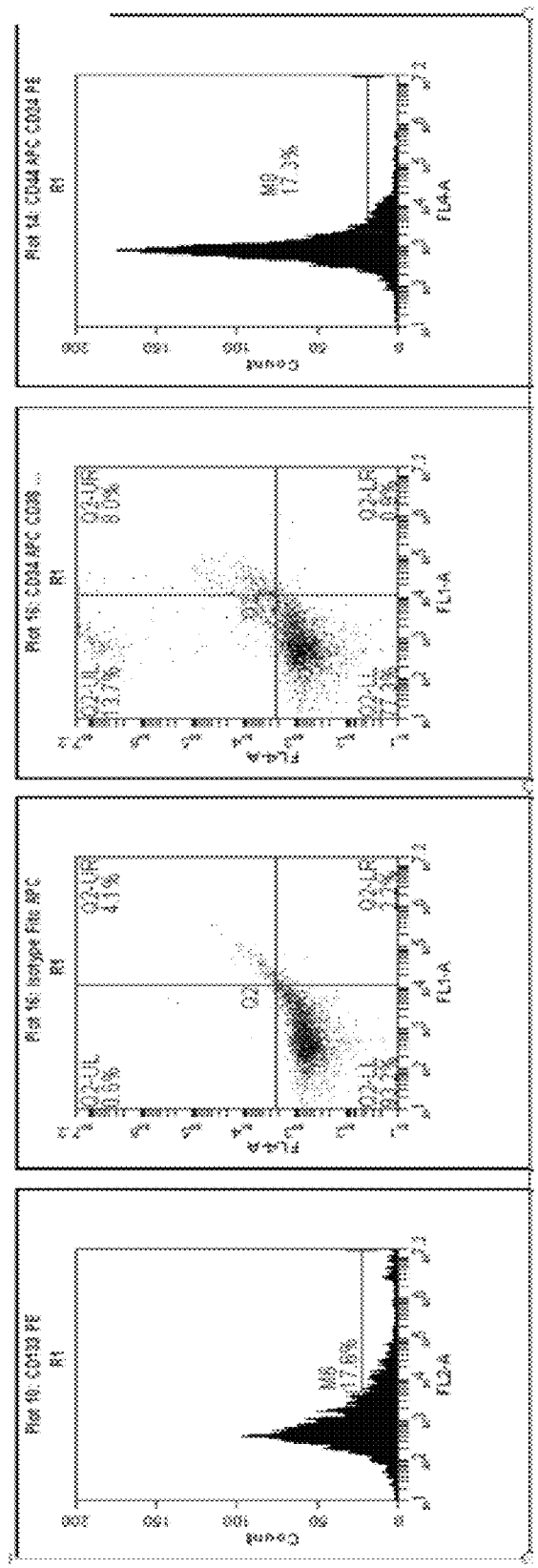
Figure 12:
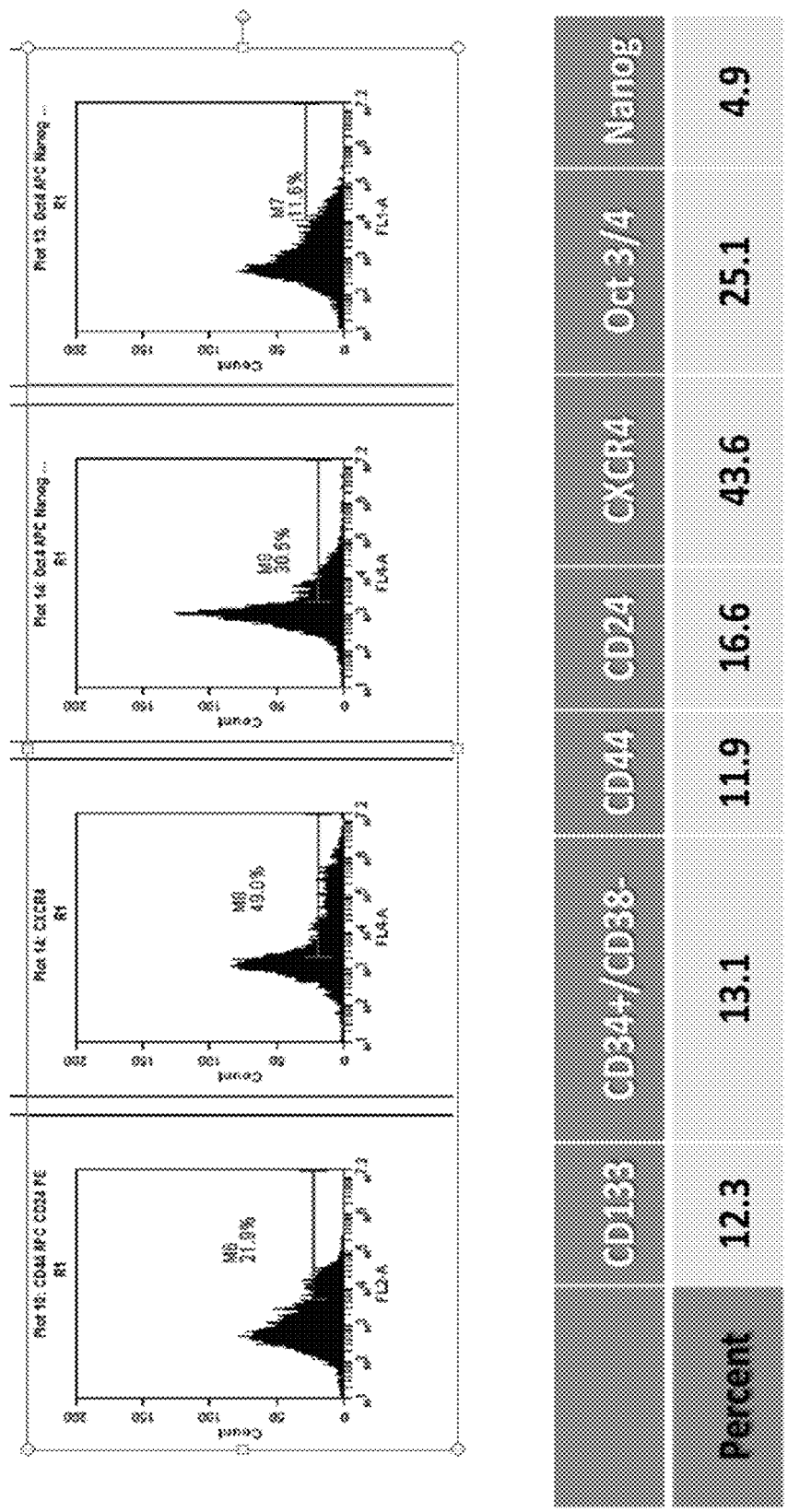

Selection of Chemotherapeutic Agent and in Subject with IDH-1 Negative Glioblastoma, WHO Grade IV A further cancer cell sample was obtained from a subject diagnosed with isocitrate dehydrogenase-1 negative glioblastoma, WHO grade IV, to further assess the ability of the presently-disclosed methodology. Again, similar to the other experiments described herein above, the glioblastoma cancer cell sample was initially cultured as a suspension and the cancer cells were immunophenotyped by flow cytometer using anti-CD133 (Milteny Biotech, Auburn, Calif.), -CD34 (Milteny Biotech, Auburn, Calif.), -CD38 (Milteny Biotech, Auburn, Calif.), -CD44 (BD Bioscience, Sparks, Md.), -CD24 (Milteny Biotech, Auburn, Calif.), -CXCR4 (Milteny Biotech, Auburn, Calif.), -OCT3/4 (BD Bioscience, Sparks, Md.), and -Nanog (BD Bioscience, Sparks, Md.). The glioblastoma cells were found positive to CD133 (12.8%) CD44 (11.9%), CD24 (16.6%), CXCR4 (43.6%), OCT3/4 (25.1%), and Nanog (4.9%) when compared to an isotype control antibody, as shown in FIG. 12. A double staining of CD34 and CD38 showed the presence of 13.1% CD34+/CD38− cells, as also shown in FIG. 12.

Figure 13:
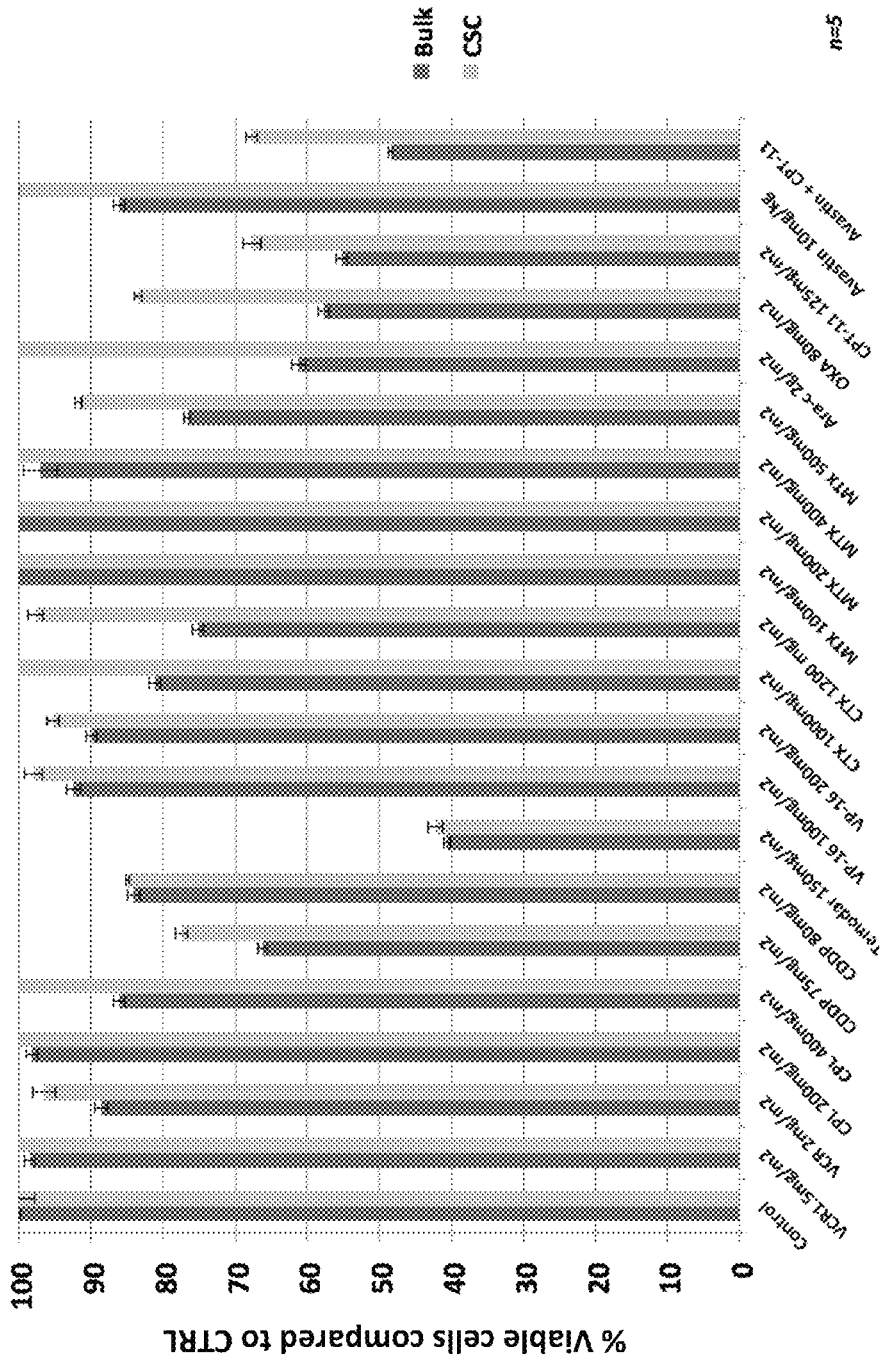
FIG. 13 is a graph showing the results of an MTT assay used to assess cell viability of bulk cancer cells and cancer stem-like cells obtained from the further IDH-1 negative glioblastoma tumor and exposed to various chemotherapeutic agents.

Then, to then expand the immature cancer stem-like cell population present within the glioblastoma primary culture, the glioblastoma cells were grown in a rotating vessel, as describe herein above and as previously described [8]. To assess the efficacy of various chemotherapeutic agents on the cancer cell sample, an MTT assay was then performed as also described herein. Upon analysis of the results from the MTT assay, and unlike the results observed in Example 4, it was observed that both the cancer stem-like cells and the bulk cancer cells were responsive to temozolomide (60% cell kill; FIG. 13), However, while the bulk cancer cells were moderately responsive (50% cell kill) to a combination of bevacizumab and CPT-11, the cancer stem-like cells were only somewhat responsive (30% cell kill) to a combination of bevacizumab and CPT-11. In this regard, the subject was then placed on temozolomide by his treating physician and the tumor subsequently regressed and the subject was in complete remission 6 months after the completion of the temozolomide therapy, to which both the cancer stem-like cells and bulk cancer cells were identified as being responsive.

Example 5

Selection of Chemotherapeutic Agent and in Subject with Medulloblastoma

Figure 14:
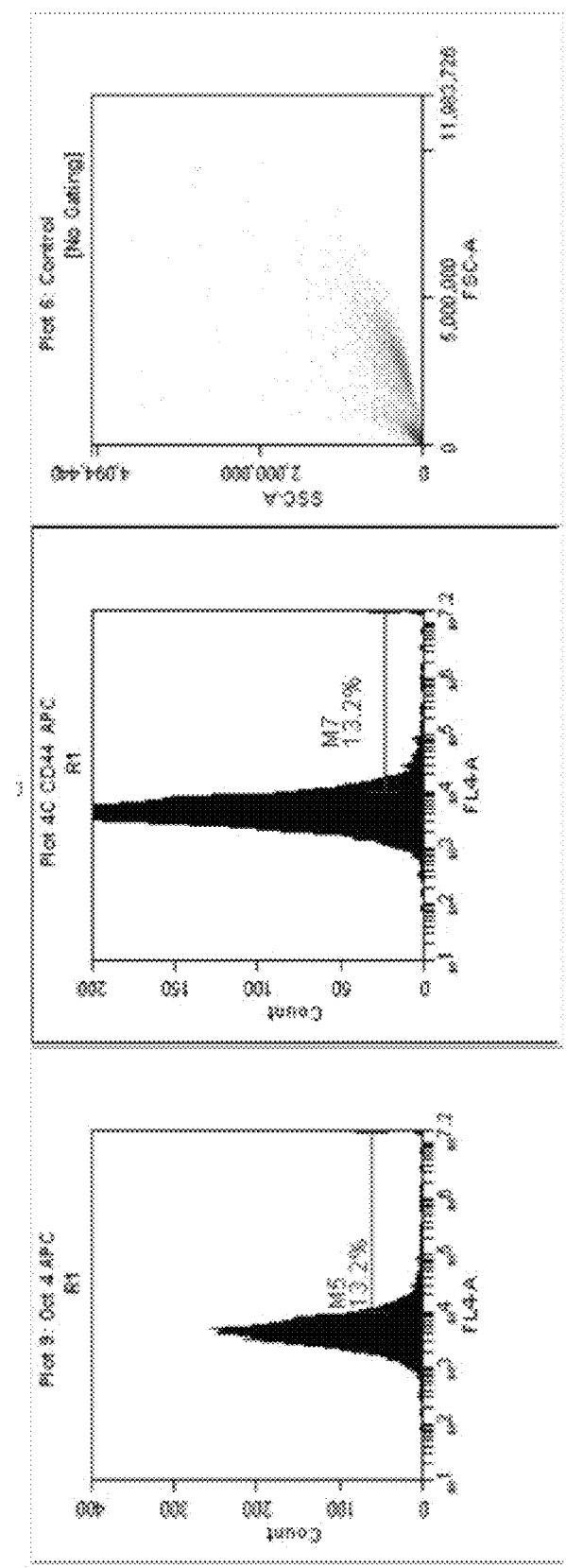
FIG. 14 includes graphs showing the immunophenotyping of cancer cells obtained from a medulloblastoma tumor using a CD133 antibody, a CD34 antibody, a CD38 antibody, a CD44 antibody, a CD117 antibody, an OCT3/4 antibody, and a Nanog antibody, and further illustrating the percent of positive cells.
Figure 14:
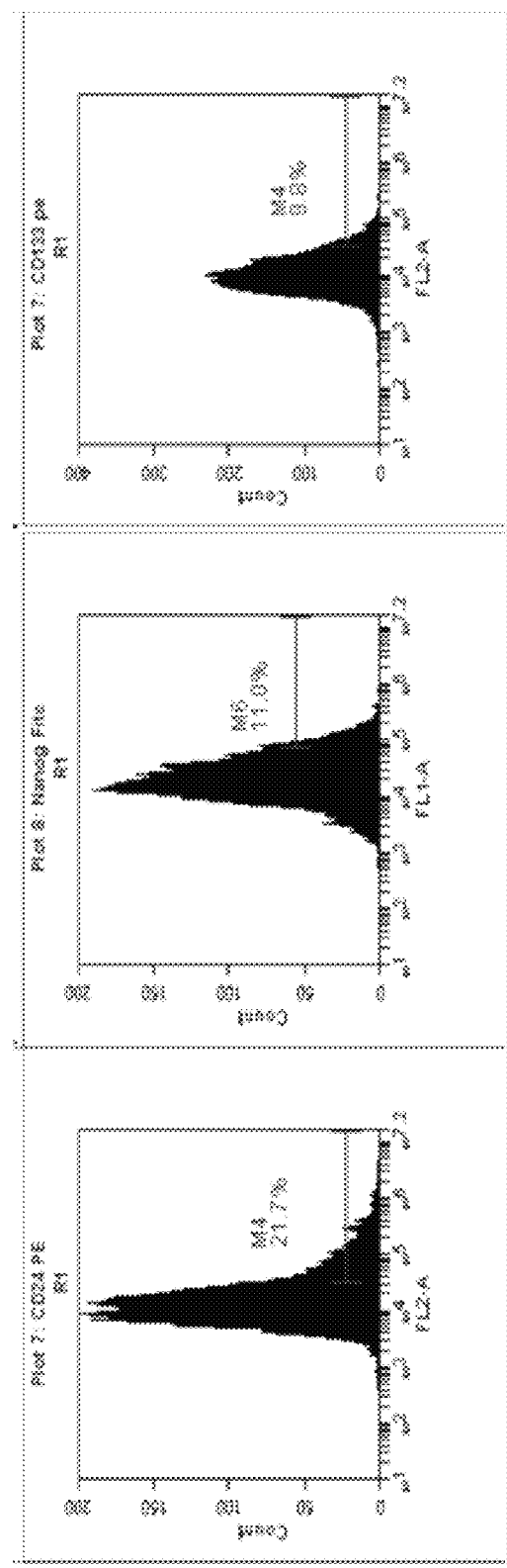
Figure 14:
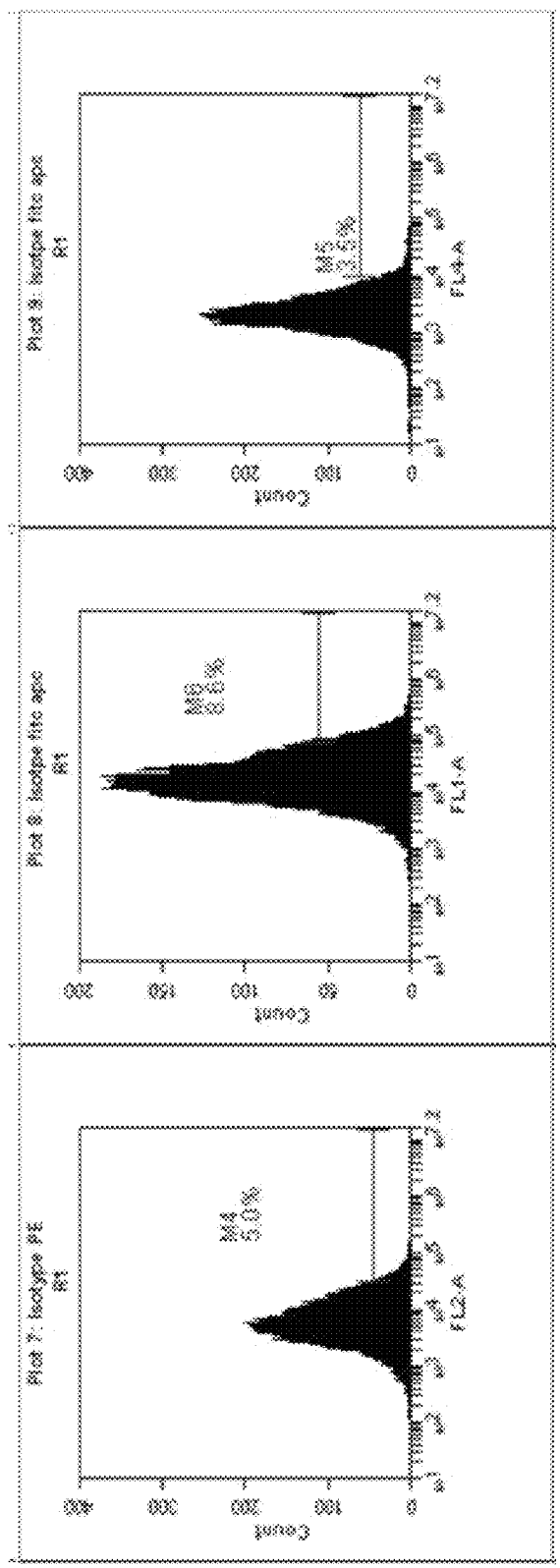
Figure 14:
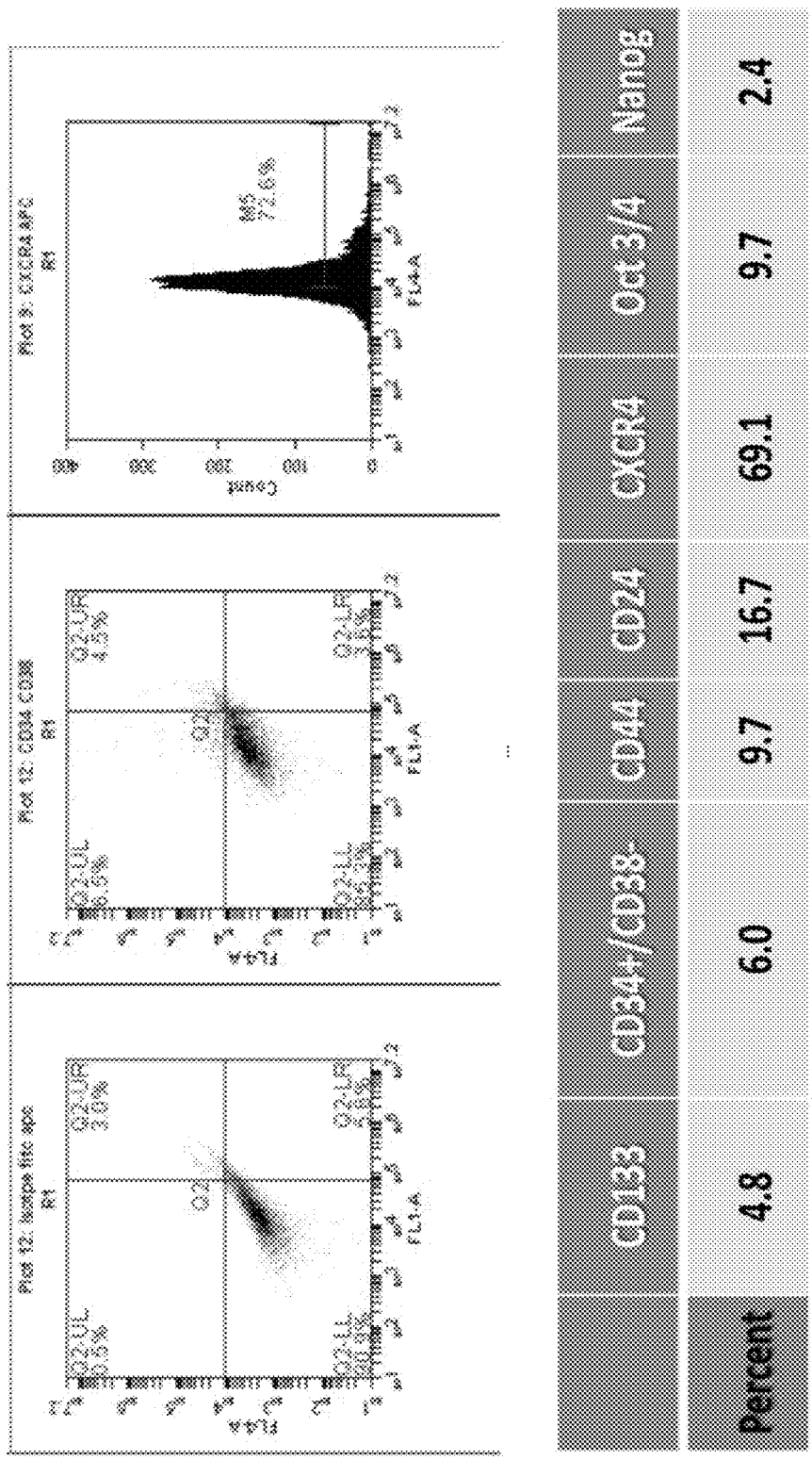

A cancer cell sample was additionally obtained from a subject diagnosed with medulloblastoma to further assess the ability of the presently-disclosed methodology. Again, similar to the other experiments described herein above, the glioblastoma cancer cell sample was initially cultured as a suspension and the cancer cells were immunophenotyped by flow cytometer using anti-CD133 (Milteny Biotech, Auburn, Calif.), -CD34 (Milteny Biotech, Auburn, Calif.), -CD38 (Milteny Biotech, Auburn, Calif.), -CD44 (BD Bioscience, Sparks, Md.), -CD24 (Milteny Biotech, Auburn, Calif.), -CXCR4 (Milteny Biotech, Auburn, Calif.), -OCT3/4 (BD Bioscience, Sparks, Md.), and -Nanog (BD Bioscience, Sparks, Md.). The glioblastoma cells were found positive to CD133 (4.8%) CD44 (6.0%), CD24 (16.7%), CXCR4 (69.1%), Oct3/4 (9.7%), and Nanog (2.4%) when compared to an isotype control antibody, as shown in FIG. 14. A double staining of CD34 and CD38 showed the presence of 6.0% CD34+/CD38− cells, as also shown in FIG. 14.

Figure 15:
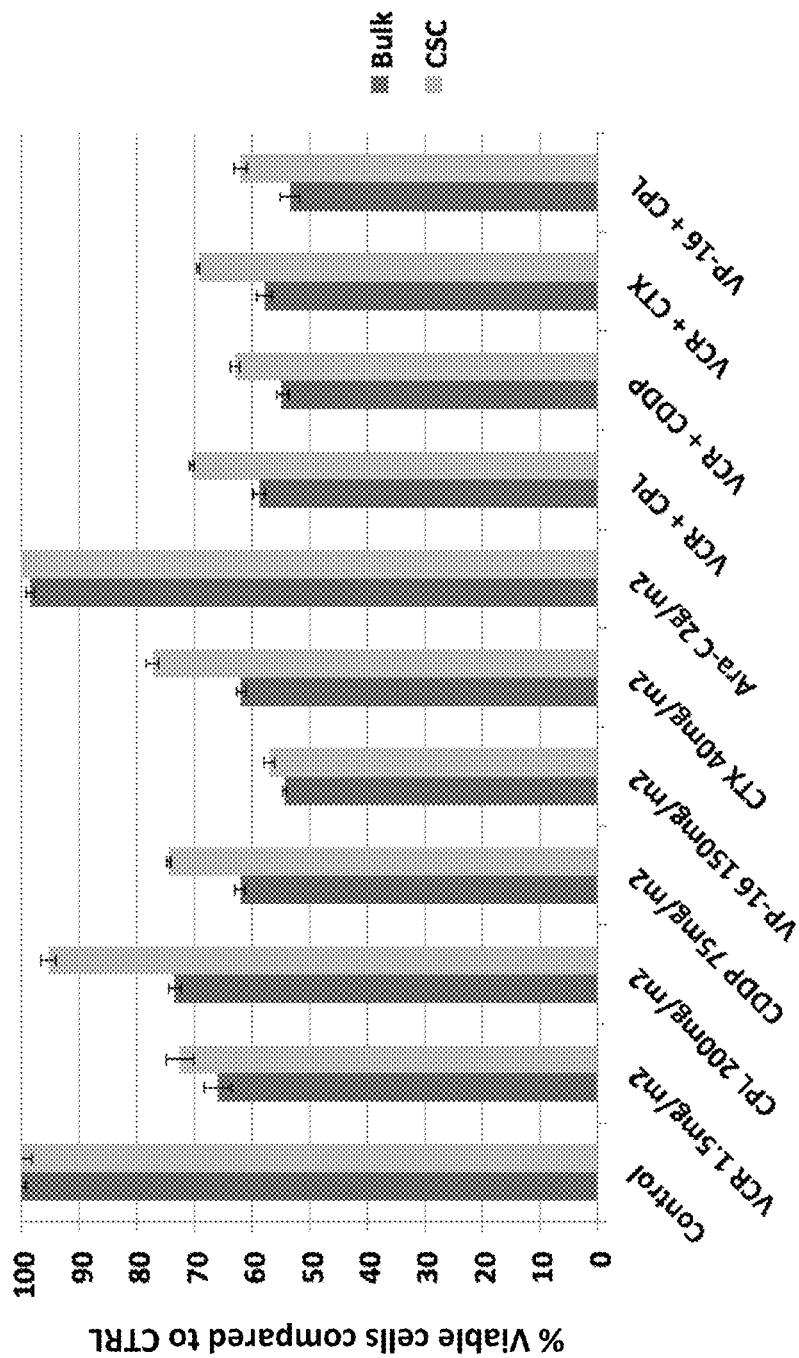
FIG. 15 is a graph showing the results of an MTT assay used to assess cell viability of bulk cancer cells and cancer stem-like cells obtained from a medulloblastoma tumor and exposed to various chemotherapeutic agents.

To then expand the immature cancer stem-like cell population present within the medulloblastoma primary culture, the medulloblastoma cells were grown in a rotating vessel, as describe herein above and as previously described [8]. To assess the efficacy of various chemotherapeutic agents on the cancer cell sample, an MTT assay was then performed as also described herein. Upon analysis of the results from the MTT assay, it was observed that a number of combinations of chemotherapeutic agents as well as VP-16 alone were effective at treating the medulloblastoma cells (FIG. 15). In this regard, the subject was then treated with various combinations of VP-16, vincristine, cisplatin, and cyclophosphamide by his treating physician, and the tumor subsequently regressed and the subject was in complete remission 6 months after the completion of the therapy.

Throughout this document, various publications, patents, and patent applications are mentioned. All such references are incorporated herein by reference, including the references set forth in the following list:

REFERENCES

1. F. Hanbali et al., Spinal cord ependymoma: radical surgical resection and outcome. *Neurosurgery* 51, 1162 (November, 2002).
2. I. S. Cooper, W. M. Craig, J. W. Kernohan, Tumors of the spinal cord; primary extramedullary gliomas. *Surg Gynecol Obstet* 92, 183 (February, 1951).
3. E. A. Iunes et al., Multifocal intradural extramedullary ependymoma. Case report. *J Neurosurg Spine* 14, 65 (January, 2011).
4. P. Dalerba et al., Phenotypic characterization of human colorectal cancer stem cells. *Proc Natl Acad Sci USA* 104, 10158 (Jun. 12, 2007).
5. L. Ricci-Vitiani et al., Identification and expansion of human colon-cancer-initiating cells. *Nature* 445, 111 (Jan. 4, 2007).
6. K. L. Chen et al., Highly enriched CD133(+)CD44 (+) stem-like cells with CD133+CD44 high metastatic subset in HCT116 colon cancer cells. *Clin Exp Metastasis* 28, 751 (December, 2011).
7. P. Aimola, V. Desiderio, A. Graziano, P. P. Claudio, Stem cells in cancer therapy: From their role in pathogenesis to their use as therapeutic agents. *Drug News Perspect* 23, 175 (April, 2010).
8. S. E. Kelly et al., Rapid selection and proliferation of CD133+ cells from cancer cell lines: chemotherapeutic implications. *PLoS One* 5, e10035 (2010).
9. B. Malik, D. Nie, Cancer stem cells and resistance to chemo and radio therapy. *Front Biosci (Elite Ed)* 4, 2142 (2012).
10. Y. Yu, G. Ramena, R. C. Elble, The role of cancer stem cells in relapse of solid tumors. *Front Biosci (Elite Ed)* 4, 1528 (2012).
11. Z. Zhang, M. S. Filho, J. E. Nor, The biology of head and neck cancer stem cells. *Oral Oncol* 48, 1 (January, 2012).
12. G. Ghiaur, J. Gerber, R. J. Jones, Concise review: cancer stem cells and minimal residual disease. *Stem Cells* 30, 89 (January, 2012).
13. J. van Meerloo, G. J. Kaspers, J. Cloos, Cell sensitivity assays: the MTT assay. *Methods Mol Biol* 731, 237 (2011).
14. T. Asazuma et al., Clinical features associated with recurrence of tumours of the spinal cord and cauda equina. *Spinal Cord* 41, 85 (February, 2003).
15. M. C. Chamberlain, T. L. Tredway, Adult primary intradural spinal cord tumors: a review. *Curr Neurol Neurosci Rep* 11, 320 (June, 2011).
16. H. Duffau, M. Gazzaz, M. Kujas, D. Fohanno, Primary intradural extramedullary ependymoma: case report and review of the literature. *Spine (Phila Pa. 1976)* 25, 1993 (Aug. 1, 2000).
17. K. H. Guppy, L. Hou, G. S. Moes, K. Sahrakar, Spinal intradural, extramedullary anaplastic ependymoma with an extradural component: Case report and review of the literature. *Surg Neurol Int* 2, 119 (2011).
18. M. D. Jenkinson et al., Outcome predictors and complications in the management of intradural spinal tumours. *Eur Spine J* 15, 203 (February, 2006).
19. S. Katoh, T. Ikata, A. Inoue, M. Takahashi, Intradural extramedullary ependymoma. A case report. *Spine (Phila Pa. 1976)* 20, 2036 (Sep. 15, 1995).
20. P. C. McCormick, K. D. Post, B. M. Stein, Intradural extramedullary tumors in adults. *Neurosurg Clin N Am* 1, 591 (July, 1990).
21. S. Pejavar et al., Pediatric intracranial ependymoma: the roles of surgery, radiation and chemotherapy. *J Neurooncol* 106, 367 (January, 2012).
22. M. Shintaku, K. Hashimoto, Anaplastic ependymoma simulating glioblastoma in the cerebrum of an adult. *Brain Tumor Pathol* 29, 31 (January, 2012).
23. D. W. Son, G. S. Song, I. H. Han, B. K. Choi, Primary extramedullary ependymoma of the cervical spine: case report and review of the literature. *J Korean Neurosurg Soc* 50, 57 (July, 2011).
24. K. W. Song et al., Surgical results of intradural extramedullary tumors. *Clin Orthop Surg* 1, 74 (June, 2009).
25. P. Tripathy, D. Mohapatra, S. Mohapatra, Primary intradural extramedullary ependymoma: report of two cases and review of the literature. *Neurol Neurochir Pol* 45, 397 (July-August, 2011).
26. W. P. Vandertop, Spinal cord ependymoma: radical surgical resection and outcome. *Neurosurgery* 53, 246; author reply 246 (July, 2003).
27. M. Reni, G. Gatta, E. Mazza, C. Vecht, Ependymoma. *Crit Rev Oncol Hematol* 63, 81 (July, 2007).
28. P. Metellus et al., Supratentorial ependymomas: prognostic factors and outcome analysis in a retrospective series of 46 adult patients. *Cancer* 113, 175 (Jul. 1, 2008).
29. Z. Kocak, M. Garipagaoglu, M. Adli, M. C. Uzal, C. Kurtman, Spinal cord ependymomas in adults: analysis of 15 cases. *J Exp Clin Cancer Res* 23, 201 (June, 2004).
30. Y. H. Lin et al., Treatment of spinal cord ependymomas by surgery with or without postoperative radiotherapy. *J Neurooncol* 71, 205 (January, 2005).
31. P. B. Volpp, K. Han, A. R. Kagan, M. Tome, Outcomes in treatment for intradural spinal cord ependymomas. *Int J Radiat Oncol Biol Phys* 69, 1199 (Nov. 15, 2007).
32. M. Reni et al., A multicenter study of the prognosis and treatment of adult brain ependymal tumors. *Cancer* 100, 1221 (Mar. 15, 2004).
33. Y. Kawabata, J. A. Takahashi, Y. Arakawa, N. Hashimoto, Long-term outcome in patients harboring intracranial ependymoma. *J Neurosurg* 103, 31 (July, 2005).
34. D. R. Gomez et al., High failure rate in spinal ependymomas with long-term follow-up. *Neuro Oncol* 7, 254 (July, 2005).
35. R. Kleinhans et al., Sensor-based cell and tissue screening for personalized cancer chemotherapy. *Med Biol Eng Comput*, (Jan. 31, 2012).
36. G. Wichmann et al., Single tissue samples from head and neck squamous cell carcinomas are representative regarding the entire tumor's chemosensitivity to cisplatin and docetaxel. *Onkologie* 32, 264 (May, 2009).
37. E. Michalova et al., [Chemosensitivity prediction in tumor cells ex vivo—difficulties and limitations of the method]. *Klin Onkol* 21, 93 (2008).
38. C. M. Kurbacher, I. A. Cree, Chemosensitivity testing using microplate adenosine triphosphate-based luminescence measurements. *Methods Mol Med* 110, 101 (2005).
39. S. L. Brower, J. E. Fensterer, J. E. Bush, The ChemoFx assay: an ex vivo chemosensitivity and resistance assay for predicting patient response to cancer chemotherapy. *Methods Mol Biol* 414, 57 (2008).
40. M. Breidenbach, D. T. Rein, P. Mallmann, C. M. Kurbacher, Individualized long-term chemotherapy for recurrent ovarian cancer after failing high-dose treatment. *Anticancer Drugs* 13, 173 (February, 2002).
41. H. Tsubouchi, S. Takao, T. Aikou, Sensitivity of human pancreatic adenocarcinoma tumor lines to chemotherapy, radiotherapy, and hyperthermia. *Hum Cell* 13, 203 (December, 2000).
42. N. Myatt et al., The ex vivo chemosensitivity profile of choroidal melanoma. *Anticancer Drugs* 8, 756 (September, 1997).

43. I. A. Cree et al., Correlation of the clinical response to chemotherapy in breast cancer with ex vivo chemosensitivity. *Anticancer Drugs* 7, 630 (August, 1996).
44. A. Biddle, I. C. Mackenzie, Cancer stem cells and EMT in carcinoma. *Cancer Metastasis Rev*, (Feb. 3, 2012).
45. Y. Bu, D. Cao, The origin of cancer stem cells. *Front Biosci (Elite Ed)* 4, 819 (2012).
46. B. Dave, V. Mittal, N. M. Tan, J. C. Chang, Epithelial-mesenchymal transition, cancer stem cells and treatment resistance. *Breast Cancer Res* 14, 202 (Jan. 19, 2012).
47. P. N. Kelly, A. Dakic, J. M. Adams, S. L. Nutt, A. Strasser, Tumor growth need not be driven by rare cancer stem cells. *Science* 317, 337 (Jul. 20, 2007).
48. K. E. Lee, M. C. Simon, From stem cells to cancer stem cells: HIF takes the stage. *Curr Opin Cell Biol*, (Jan. 30, 2012).
49. Y. Li, J. Laterra, Cancer stem cells: distinct entities or dynamically regulated phenotypes? *Cancer Res* 72, 576 (Feb. 1, 2012).
50. L. V. Nguyen, R. Vanner, P. Dirks, C. J. Eaves, Cancer stem cells: an evolving concept. *Nat Rev Cancer* 12, 133 (2012).
51. M. Skinner, Cancer stem cells: TAZ takes centre stage. *Nat Rev Cancer* 12, 82 (2012).
52. S. L. Suchy, L. M. Hancher, D. Wang, P. R. Ervin, Jr., S. L. Brower, Chemoresponse assay for evaluating response to sunitinib in primary cultures of breast cancer. *Cancer Biol Ther* 11, 1059 (Jun. 15, 2011).
53. W. K. Huh et al., Consistency of in vitro chemoresponse assay results and population clinical response rates among women with endometrial carcinoma. *Int J Gynecol Cancer* 21, 494 (April, 2011).
54. S. D. Rice et al., An in vitro chemoresponse assay defines a subset of colorectal and lung carcinomas responsive to cetuximab. *Cancer Biol Ther* 11, 196 (Jan. 15, 2011).
55. S. D. Rice et al., Analysis of chemotherapeutic response heterogeneity and drug clustering based on mechanism of action using an in vitro assay. *Anticancer Res* 30, 2805 (July, 2010).
56. K. S. Ballard, S. S. Tedjarati, W. R. Robinson, H. D. Homesley, E. L. Thurston, Embryonal rhabdomyosarcoma: adjuvant and ex vivo assay-directed chemotherapy. *Int J Gynecol Cancer* 20, 561 (May, 2010).
57. S, N. Cross et al., Differential sensitivity to platinum-based chemotherapy in primary uterine serous papillary carcinoma cell lines with high vs low HER-2/neu expression in vitro. *Am J Obstet Gynecol* 203, 162 e1 (August, 2010).
58. T. J. Herzog, T. C. Krivak, A. N. Fader, R. L. Coleman, Chemosensitivity testing with ChemoFx and overall survival in primary ovarian cancer. *Am J Obstet Gynecol* 203, 68 e1 (July, 2010).
59. Z. Mi et al., Feasibility assessment of a chemoresponse assay to predict pathologic response in neoadjuvant chemotherapy for breast cancer patients. *Anticancer Res* 28, 1733 (May-June, 2008).
60. H. Gallion et al., Progression-free interval in ovarian cancer and predictive value of an ex vivo chemoresponse assay. *Int J Gynecol Cancer* 16, 194 (January-February, 2006).
61. D. Peters, J. Freund, R. L. Ochs, Genome-wide transcriptional analysis of carboplatin response in chemosensitive and chemoresistant ovarian cancer cells. *Mol Cancer Ther* 4, 1605 (October, 2005).
62. R. L. Ochs, D. Burholt, P. Kornblith, The ChemoFx assay: an ex vivo cell culture assay for predicting anticancer drug responses. *Methods Mol Med* 110, 155 (2005).
63. R. B. Ness, S. R. Wisniewski, H. Eng, W. Christopherson, Cell viability assay for drug testing in ovarian cancer: in vitro kill versus clinical response. *Anticancer Res* 22, 1145 (March-April, 2002).

What is claimed is:

1. A method for identifying one or more chemotherapeutic agents for treating a cancer, comprising:
   providing a cancer cell sample including a population of bulk cancer cells and a population of cancer stem-like cells;
   culturing a first portion of the cancer cell sample in a hydrodynamic focusing bioreactor under microgravity conditions and for a period of time sufficient to selectively increase the number of cancer stem-like cells;
   contacting the population of cancer stem-like cells with one or more chemotherapeutic agents; and
   detecting whether the one or more chemotherapeutic agents are cytotoxic or not to the cancer stem-like cell, thereby identifying the one or more chemotherapeutic agents.

2. The method of claim 1, further comprising the step of identifying a type of bulk cancer cells present in the cancer cell sample such that the one or more chemotherapeutic agents are further selected based on the type of bulk cancer cells present in the cancer cell sample.

3. The method of claim 1, further comprising the steps of:
   culturing a second portion of the cancer cell sample under conditions and for a period of time sufficient to increase the number of bulk cancer cells;
   contacting the bulk cancer cells with the one or more chemotherapeutic agents; and
   detecting whether the one or more chemotherapeutic agents are cytotoxic or not to the bulk cancer cells;
   wherein the one or more chemotherapeutic agents selected for treating the cancer are cytotoxic to both the cancer stem-like cells and the bulk cancer cells.

4. The method of claim 1, wherein culturing the first portion of the cancer cell sample comprises inoculating about $1 \times 10^6$ cells.

5. The method of claim 3, wherein culturing the second portion of the cancer cell sample comprises inoculating about $1 \times 10^6$ cells.

6. The method of claim 1, further comprising immunophenotyping the cancer cell sample to identify a type of cancer cell in the cancer cell sample.

7. The method of claim 6, wherein the step of immunophenotyping the cancer cell sample is performed by flow cytometry using one or more antibodies against the cancer cell sample.

8. The method of claim 7, wherein the one or more antibodies are against CD24, CD34, CD38, CD44, CD133, CXCR4, OCT3/4, Nanog, or combinations thereof.

9. The method of claim 1, wherein the step of contacting the cancer stem-like cells with the one or more chemotherapeutic agents comprises contacting the cancer stem-like cells with the one or more chemotherapeutic agents for a time period of about one hour.

10. The method of claim 1, wherein the step of detecting whether the one or more chemotherapeutic agents are cytotoxic to the cancer stem-like cells comprises calculating a percentage of non-viable cancer stem-like cells.

11. The method of claim 10, wherein the percentage of non-viable cancer stem-like cells is calculated using an assay selected from the group consisting of an MTT assay, a ALAMARBLUE Assay and a WST-8 assay.

12. The method of claim 1, wherein the cancer cell sample comprises a solid cancer cell sample, a liquid cancer cell sample, or combinations thereof.

13. The method of claim 12, wherein the solid cancer cell sample comprises a lung cancer cell sample, a breast cancer cell sample, a central nervous system cancer cell sample, a colon cancer cell sample, a lymph node cancer cell sample, or combinations thereof.

14. The method of claim 12, where the liquid cancer cell sample comprises a leukemia cell sample, a lymphoma cell sample, or a myeloma cell sample.

15. The method of claim 1, wherein the one or more chemotherapeutic agents are selected from the group consisting of cisplatin, oxaliplatin, arabinoside-C, VP-16, busulfan, methotrexate, CPT-11, temozolomide, and combinations thereof.

16. The method of claim 1, wherein the cancer cell sample is an ependymoma cell sample.

17. The method of claim 1, wherein the step of contacting the cancer stem-like cells with the one or more chemotherapeutic agents comprises contacting the cancer stem-like cells with a predetermined concentration of the one or more chemotherapeutic agents; and
wherein the predetermined concentration of the one or more chemotherapeutic agents comprises a concentration below a clinically relevant dosage, equal to the clinically relevant dosage, or above the clinically relevant dosage.

18. A method of treating a cancer in a subject in need thereof, comprising:
providing a cancer cell sample from the subject, the cancer cell sample including a population of bulk cancer cells and a population of cancer stem-like cells;
culturing a first portion of the cancer cell sample in a hydrodynamic focusing bioreactor under microgravity conditions and for a period of time sufficient to selectively increase the number of cancer stem-like cells and selectively kill the population of bulk cancer cells;
contacting the cancer stem-like cells with one or more chemotherapeutic agents;
detecting whether the one or more chemotherapeutic agents are cytotoxic or not to the cancer stem-like cells;
identifying the one or more chemotherapeutic agents for treating the cancer if there is an increase in an amount of cytotoxicity; and
administering the one or more selected chemotherapeutic agents to the subject.

19. The method of claim 18, further comprising the step of identifying a type of bulk cancer cell present in the cancer cell sample such that the one or more chemotherapeutic agents are further selected based on the type of bulk cancer cell present in the cancer cell sample.

20. The method of claim 18, further comprising the steps of:
culturing a second portion of the cancer cell sample under conditions and for a period of time sufficient to enhance the bulk cancer cells;
contacting the bulk cancer cells with the one or more chemotherapeutic agents; and
detecting whether the one or more chemotherapeutic agents are cytotoxic or not to the bulk cancer cells;
wherein the one or more chemotherapeutic agents administered to the subject are cytotoxic to both the cancer stem-like cells and the bulk cancer cells.

21. The method of claim 18, wherein culturing the first portion of the cancer cell sample comprises inoculating about $1 \times 10^6$ cells.

22. The method of claim 20, wherein culturing the second portion of the cancer cell sample comprises inoculating about $1 \times 10^6$ cells.

23. The method of claim 18, further comprising immunophenotyping the cancer cell sample to identify a type of cancer cell in the cancer cell sample.

24. The method of claim 23, wherein the step of immunophenotyping the cancer cell sample is performed by flow cytometry using one or more antibodies against the cancer stem-like cells.

25. The method of claim 24, wherein the one or more antibodies are against CD24, CD34, CD38, CD44, CD133, CXCR4, OCT3/4, Nanog, or combinations thereof.

26. The method of claim 18, wherein the step of contacting the cancer stem-like cells with the one or more chemotherapeutic agents comprises contacting the cancer stem-like cells with the one or more chemotherapeutic agents for a time period of about one hour.

27. The method of claim 18, wherein the step of detecting whether the one or more chemotherapeutic agents are cytotoxic to the cancer stem-like cells comprises calculating a percentage of non-viable cancer stem-like cells.

28. The method of claim 27, wherein the percentage of non-viable cancer stem-like cells is calculated using an assay selected from the group consisting of an MTT assay, a ALAMARBLUE assay and a WST-8 assay.

29. The method of claim 18, wherein the cancer cell sample comprises a solid cancer cell sample, a liquid cancer cell sample, or combinations thereof.

30. The method of claim 29, wherein the solid cancer cell sample comprises a lung cancer cell sample, a breast cancer cell sample, a central nervous system cancer cell sample, a colon cancer cell sample, a lymph node cancer cell sample, or combinations thereof.

31. The method of claim 29, where the liquid cancer cell sample comprises a leukemia cell sample, a lymphoma cell sample, or a myeloma cell sample.

32. The method of claim 18, wherein the one or more chemotherapeutic agents are selected from the group consisting of cisplatin, oxaliplatin, arabinoside-C, VP-16, busulfan, methotrexate, CPT-11, temozolomide, and combinations thereof.

33. The method of claim 18, wherein the cancer cell sample is an ependymoma cell sample.

34. The method of claim 18, wherein the step of contacting the cancer stem-like cells with the one or more chemotherapeutic agents comprises contacting the cancer stem-like cells with a predetermined concentration of the one or more chemotherapeutic agents; and
wherein the predetermined concentration of the one or more chemotherapeutic agents comprises a concentration below a clinically relevant dosage, equal to the clinically relevant dosage, or above the clinically relevant dosage.

35. A method of identifying a compound useful for treating a cancer, comprising:
providing a cancer cell sample including a population of bulk cancer cells and a population of cancer stem-like cells;
culturing the cancer cell sample in a hydrodynamic focusing bioreactor under microgravity conditions and for a period of time sufficient to selectively increase the number of cancer stem-like cells;
contacting the population of cancer stem-like cells with an effective amount of a test compound;
detecting whether the test compound is cytotoxic to the cancer stem-like cells or not; and identifying the test compound as a compound useful for treating cancer if there is an increase in cytotoxicity.

36. The method of claim 1, further comprises identifying the one or more chemotherapeutic agents as having an effect on the cancer cell sample if there is an increase in an amount of cytotoxicity of the cancer stem-like cells.

37. The method of claim 1, wherein culturing a first population of the cancer cell sample selectivity kills the population of bulk cancer cells.

* * * * *